(12) United States Patent
Seibel

(10) Patent No.: US 9,670,505 B2
(45) Date of Patent: Jun. 6, 2017

(54) MITOCHONDRIAL EXPRESSION VECTOR AND METHOD FOR THE TRANSFORMATION OF MITOCHONDRIA

(71) Applicant: UNIVERSITAT LEIPZIG, Leipzig (DE)

(72) Inventor: Peter Seibel, Uettingen (DE)

(73) Assignee: UNIVERSITAT LEIPZIG, Leipzig (DE)

( * ) Notice: Subject to any disclaimer, the term of this patent is extended or adjusted under 35 U.S.C. 154(b) by 0 days.

(21) Appl. No.: 14/669,397

(22) Filed: Mar. 26, 2015

(65) Prior Publication Data

US 2015/0315608 A1    Nov. 5, 2015

Related U.S. Application Data

(63) Continuation-in-part of application No. PCT/EP2013/002879, filed on Sep. 25, 2013.

(30) Foreign Application Priority Data

Sep. 26, 2012    (EP) .................................... 12006716

(51) Int. Cl.
| | | |
|---|---|---|
| C12N 5/02 | (2006.01) | |
| C12N 5/00 | (2006.01) | |
| C12N 15/00 | (2006.01) | |
| C12N 15/85 | (2006.01) | |

(52) U.S. Cl.
CPC ........ *C12N 15/85* (2013.01); *C12N 2800/107* (2013.01); *C12N 2820/60* (2013.01)

(58) Field of Classification Search
None
See application file for complete search history.

(56) References Cited

U.S. PATENT DOCUMENTS

| | | |
|---|---|---|
| 7,279,326 B2 | 10/2007 | Weissig et al. |
| 9,017,999 B2 | 4/2015 | Corral-Debrinski et al. |
| 2009/0306188 A1 | 12/2009 | Corral-Debrinski et al. |
| 2011/0166195 A1 | 7/2011 | Seibel |
| 2014/0377869 A1 | 12/2014 | Corral-Debrinski et al. |
| 2015/0087054 A1 | 3/2015 | Corral-Debrinski et al. |
| 2015/0225740 A1 | 8/2015 | Corral-Debrinski et al. |

FOREIGN PATENT DOCUMENTS

| | | |
|---|---|---|
| WO | 2006/117250 | 11/2006 |
| WO | 2010/003540 | 1/2010 |

OTHER PUBLICATIONS

Kim et al. Mammalian cell transfection: the present and the future. 2010. Anal. Bioanal. Chem., vol. 397, pp. 3172-3178.*
Wakabayashi et al. Megamitochondria formation—physiology and pathology. 2002. J. Cell. Mol. Med., vol. 6, No. 4, pp. 497-538.*
International Search Report dated Jan. 7, 2014, which issued during prosecution of International Application No. PCT/EP2013/002879. 4 pages.
Johnson, et al. "Mitochondrial transformation in yeast by bombardment with microprojectiles" Science 240 (4858):1538-1541.

* cited by examiner

*Primary Examiner* — Channing S Mahatan
(74) *Attorney, Agent, or Firm* — Vedder Price P.C.; Thomas J. Kowalski; Deborah L. Lu

(57) ABSTRACT

The invention relates to a mitochondrial expression vector which may comprise a gene to be expressed and/or a selection marker and a mitochondrial region, and a method for inserting a DNA to be expressed into mitochondria of mammalian cells, wherein the method may comprise the steps: (i) construction of a mitochondrial expression vector or a mitochondrial genome, (ii) reversible induction of megamitochondria and (iii) transfection of the megamitochondria by means of a physical transfection method.

7 Claims, 20 Drawing Sheets

Figure 26A

```
  1 AUGGUAUCCAAAGGCGAAGAACUAUUCACCGGCGUAGUACCCAUCCUAGUAGAACUAGAC  60
    M  V  S  K  G  E  E  L  F  T  G  V  V  P  I  L  V  E  L  D

61 GGCGACGUAAACGGACACAAAUUCUCCGUAUCCGGCGAAGGCGAAGGCGACGCCACCUAC 120
    G  D  V  N  G  H  K  F  S  V  S  G  E  G  E  G  D  A  T  Y

121 GGCAAACUAACCCUAAAAUUCAUUUGCACCACCGGCAAACUACCCGUACCCUGACCCACC 180
    G  K  L  T  L  K  F  I  C  T  T  G  K  L  P  V  P  W  P  T

181 CUAGUAACCACCCUAACCUACGGCGUACAAUGCUUCUCCCGAUACCCCGACCACUAAAA  240
    L  V  T  T  L  T  Y  G  V  Q  C  F  S  R  Y  P  D  H  M  K

241 CAACACGACUUCUUCAAAUCCGCCAUACCCGAAGGCUAUGUCCAAGAACGAACCAUCUUC 300
    Q  H  D  F  F  K  S  A  M  P  E  G  Y  V  Q  E  R  T  I  F

301 UUCAAAGACGACGGCAACUACAAAACACGAGCCGAAGUAAAAUUCGAGGGCGACACCCUA 360
    F  K  D  D  G  N  Y  K  T  R  A  E  V  K  F  E  G  D  T  L

361 GUAAACCGAAUCGAACUAAAAGGCAUCGACUUCAAAGAGGACGGCAACAUCCUAGGCCAC 420
    V  N  R  I  E  L  K  G  I  D  F  K  E  D  G  N  I  L  G  H

421 AAACUAGAAUACAACUACAACUCCCACAACGUCUAUAUCAUAGCCGACAAACAAAAAAAC 480
    K  L  E  Y  N  Y  N  S  H  N  V  Y  I  M  A  D  K  Q  K  N

481 GGCAUCAAAGUAAACUUCAAAAUCCGACACAACAUCGAGGACGGCUCCGUACAACUAGCC 540
    G  I  K  V  N  F  K  I  R  H  N  I  E  D  G  S  V  Q  L  A

541 GACCACUACCAACAAAACACCCCCAUCGGCGACGGCCCCGUACUACUACCCGACAACCAC 600
    D  H  Y  Q  Q  N  T  P  I  G  D  G  P  V  L  L  P  D  N  H

601 UACCUAUCCACCCAAUCCGCCCUAUCCAAAGACCCCAACGAAAAACGCGAUCACAUGGUC 660
    Y  L  S  T  Q  S  A  L  S  K  D  P  N  E  K  R  D  H  M  V
```

```
661 CUACUAGAGUUCGUAACCGCCGCAGGCAUCACCCUAGGCAUAGACGAACUAUACAAAUAA 720
     L  L  E  F  V  T  A  A  G  I  T  L  G  N  D  E  L  Y  K  *
```

Figure 26B

MITOCHONDRIAL EXPRESSION VECTOR AND METHOD FOR THE TRANSFORMATION OF MITOCHONDRIA

RELATED APPLICATIONS AND INCORPORATION BY REFERENCE

This application is a continuation-in-part application of international patent application Serial No. PCT/EP2013/002879 filed 25 Sep. 2013, which published as PCT Publication No. WO 2014/048565 on 3 Apr. 2014, which claims benefit of European patent application Serial No. 12006716.0 filed 26 Sep. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Mar. 15, 2016, is named 48171.00.2001_SL.txt and is ~5,284 bytes in size.

FIELD OF THE INVENTION

The present invention relates to a mitochondrial expression vector and methods for introducing exogenous DNA into mitochondria of mammalian cells.

INTRODUCTION

Mitochondrial diseases or mitochondriopathies result in a failure of the cellular energy metabolism and nowadays play an important part in pediatric and neurologic clinics, wherein it is still difficult to assess the prevalence of these diseases (about 1:5000, Friedrich-Baur-Institut).

Mitochondriopathies are very often accompanied by typical symptoms, including: muscle weakness, deteriorated vision up to blindness, epileptic seizures and vertigos.

Due to their key position in the aerobic metabolism of the cell, a disorder of the mitochondria function usually results in a clinical mixed picture with multi-organ involvement, where in particular the tissues with high energy requirement are affected. These are the central nervous system (seizure, ataxia, leukodystrophy, Leigh Syndrome, mental retardation), the muscles (myopathy, muscle pain, cardiomyopathy, external ophthalmoplegia), the endocrine organs (hypothyroidism, hypoparathyroidism, type I diabetes mellitus), the liver (acute liver failure, liver cirrhosis), the sensory organs (nervus opticus atrophy, retinitis pigmentosa, inner ear hearing loss), the bone marrow (non-regenerative anemia) and the kidneys (kidney insufficiency, Fanconi syndrome).

The most important mitochondriopathies are listed below and are referred to by acronyms on the basis of the symptoms. MELAS: "mitochondrial encephalopathy, lactic acidosis and apoplexy-like episodes", MERRF: "myoclonic epilepsy with ragged red fibers", NARP: "neuropathy, ataxia, retinitis pigmentosa", CPEO: "chronically progressive external ophthalmoplegia (paralysis of the external eye muscles), KSS: "Kearns Sayre syndrome" (a special variant of the CPEO, multi-systemic disease) and LHON: "Leber's hereditary optic neuropathy" (Leitlinien Pädiatrie, A13, Mitochondriale Erkrankungen, Schuelke, M., as per December 2010, Elsevier GmbH, Munich; Finsterer, J., Eur. J. Paediatr. Neurol., 2010, 14: 29-44).

Causes can be genetically conditioned defects in the pyruvate dehydrogenase, the pyruvate carboxylase, in the proteins of the citric acid cycle, in respiratory chain complexes I to IV or the ATP transport proteins, wherein further genetic defects may concern proteins or protein complexes which are involved in the regulation of the mitochondrial replication, transcription or the translation.

Since the above mentioned proteins are encoded by both the mitochondrial DNA (mtDNA; maternal inheritance) and the nuclear genome (nDNA; Mendelian inheritance), mutations in the two genomes can trigger these diseases. However, modifications in the mitochondrial DNA cannot be corrected to date—in contrast to the nuclear genome—, and therefore only the symptoms and not the triggers can be treated in a large number of mitochondrial diseases. For example, mitochondrial diseases are treated by administering substances which have an effect on the metabolism (e.g. cofactors of respiratory chain enzymes) and which shall compensate for the defects in the oxidative metabolism. However, this form of therapy could achieve a marked improvement of the state of health of the patient only in exceptional cases, wherein healing on the basis of therapy approaches which are based on the treatment of symptoms cannot be expected (Chinnery, P. F. and D. M. Turnbull, Am. J. Med. Genet., 2001, 106: 94-101). Therefore, therapies which focus on the trigger factor of the disease have to be regarded as more promising.

The somatic gene therapy is a possible form of therapy of mitochondrial diseases, which corrects the genetic defect of the mitochondrial DNA. For this purpose, the moiety of the mutated mtDNA should be forced below the threshold value necessary for the development of clinical symptoms to enable the restoration of the normal phenotype. However, a complete removal of the mutated DNA would be ideal.

A somatic gene therapy can be conducted by means of different strategies: competition with the mutated genes by introducing intact replicative and transcriptionally active genes; exchange of the mutated genes with intact genes by recombination; inhibition of the replication of mutated mtDNA by antisense oligonucleotides; and degradation of mutated mtDNA.

However, the first three strategies rely on the transport of nucleic acids into the mitochondria, which has been a major obstacle so far. The active transport of nucleus-encoded RNAs and tRNAs into the mitochondria is known for yeasts (Martin, R. P. et al., Biochemistry, 1979, 18: 4600-4605), protozoa (Simpson L. and J. Shaw, Cell, 1989, 57: 355-366) and plants (Gray, M. W. and Boer, P. H., Philos. Trans. R. Soc. London B Biol. Sci., 1988, 319: 135-147). The import of a yeast tRNA was also documented with separated human mitochondria (Entelis, N. S. et al., J. Biol. Chem., 2001, 276: 45642-45653). However, it has not been possible thus far to prove the import of relatively large nucleic acids into mammalian mitochondria in vivo.

A possibility consists in the use of physical transformation methods. For example, DNA has already been introduced into the mitochondria by electroporation but these mitochondria had been separated from the cells beforehand (Collombet, J. M. et al., J. Biol. Chem., 1997, 272: 5342-5347). Another physical method used was the gene gun or particle gun method where gold or tungsten microprojectiles are used to introduce DNA into cells. The DNA is here bound to the particle surface and can be released again at the destination. The transformation of chloroplasts into plants already uses this method successfully (Kanevski, I. and P. Maliga, Proc. Natl. Acad. Sci., 1994, 91: 1969-1973; Barone, P. et al., J. Exp. Bot., 2009, 60: 3195-3202; De Marchis, F. et al., Transgenic Res., 2009, 18: 17-30). The transformation of chloroplasts and mitochondria was also successful in the case of spongeweed, *Chlamydomonas reinhardtii* (Boynton, J. E. et al., Science, 1988, 240: 1534-1538; Yamasaki, T. et al., Plant Mol. Biol., 2005, 58: 515-527; Remacle, C. et al., Proc. Natl. Acad. Sci. U.S.A., 2006, 103: 4771-4776). In yeast cells, mitochondria could also be loaded with exogenous DNA by means of the gene gun (Fox, T. D. et al., Proc. Natl. Acad. Sci. U.S.A., 1988, 85: 7288-7292; Johnston, S. A. et al., Science, 1988, 240: 1538-1541; Sulo, P. et al., Nucleic Acid Res., 1995, 23: 856-860; Meunier, B., Biochem. J., 2001, 354: 407-412).

These positive results are based on the fact that compared to mitochondria the target organelles in the employed organisms are very large in mammalian cells. Since the employed particles have a diameter of at least 0.3 µm, it is, however, almost impossible to penetrate the small mitochondria of mammalian cells without destroying them. Due to this problem, another physical transformation method, i.e. the microinjection, cannot be realized in mitochondria thus far.

The patent application PCT/EP2009/004454 relates to an in vitro method for the reversible induction of megamitochondria, wherein the mammalian cells grow in a culture medium acidified with lactic acid to give a pH of between 5.6 and 6.7 so as to form metamitochondria. These megamitochondria are larger than non-induced mitochondria, and therefore it is postulated that they can be penetrated without destroying them. However, the description of patent application PCT/EP2009/004454 is limited to the method of reversibly inducing megamitochondria, and the transfection and the use thereof for examining or treating mitochondriopathies is only postulated. In addition, the induction by means of lactic acid merely results in the formation of megamitochondria having maximum diameters of 2-3 µm, which are smaller than the average size of a cell nucleus, thus failing to provide ideal preconditions for the transfection by means of a physical transfection method, e.g. microinjection.

U.S. Pat. No. 7,279,326 B2 relates to a composition and a method for introducing a wild type (wt) mitochondrial DNA (mtDNA) molecule into a mammalian cell, wherein the wt-mtDNA molecule has a mitochondrial leader sequence peptide (MLS) to facilitate the incorporation of the mtDNA molecule into a mitochondrion of the mammalian cell.

The international patent application with publication number WO 2006/117250 A2 shows that the mRNA sorting to the mitochondrial surface is an effective option to carry out an allotopic expression, wherein the mRNA sorting can be controlled by the selection of suitable mitochondrial signal sequences (mitochondrion targeting sequence, MTS) and suitable 3'UTR sequences. The CDS sequence which codes for the protein that shall be introduced into the mitochondrion, is guided by these suitable MTS and 3'UTR sequences from the cell nucleus compartment to mitochondrion-bound polysomes where it assists in the effective translocation of a functioning protein into the mitochondrion.

The publication Johnston, S. A. et al. (Science, 1988, 240: 1538-1541) presents the "biolistic" (biologically ballistic) method for introducing DNA into yeast cells for the stable transformation of the mitochondria thereof. In this connection, the cells were bombarded with DNA-coated tungsten microprojectiles, wherein transformants were obtained which had incorporated the DNA sequences at their homologous site.

The international patent application with publication number WO 2010/003540 A2 relates to an in vitro method for forming megamitochondria in cells, wherein the cells were grown in a suitable fermentation medium which had been acidified to a pH between 5.3 and 6.7 using lactic acid. Furthermore, the application relates to $H^+$-ionophores which catalyze the electroneutral exchange of $K^+$ with $H^+$, and to inhibitors of the actin polymerization for preventing a disease where the inhibition or reduction in the formation of megamitochondria has a favorable effect.

Citation or identification of any document in this application is not an admission that such document is available as prior art to the present invention.

SUMMARY OF THE INVENTION

Therefore, a problem of the present invention is to provide a mitochondrial expression vector and a method for introducing exogenous DNA into mitochondria of mammalian cells.

A solution of the above mentioned technical problem is in particular the provision of a mitochondrial expression vector and physical transfection methods, by means of which exogenous DNA that is integrated in a mitochondrial expression vector, is introduced in vivo or in vitro into the mitochondria of mammalian cells, wherein the mitochondria are induced to give megamitochondria prior to the application of the physical transfection method.

Thus, the present invention initially provides mitochondrial expression vectors which can be used for incorporating exogenous DNA and which are able to express the exogenous DNA exclusively in mitochondria.

Furthermore, the subject matter of the present invention relates to an improved method for the reversible induction of megamitochondria since the reversible induction of the present invention results in megamitochondria having diameters which are larger than the average size of the cell nucleus, i.e. have a size of up to 10 µm. Thus, the present invention provides ideal preconditions for the transfection by means of a physical transfection method, e.g. microinjection.

In addition, physical transfection methods are disclosed, by means of which it is possible to transfect megamitochondria of mammalian cells.

Furthermore, the present invention provides a method for introducing exogenous DNA into mitochondria of mammalian cells, which may comprise the steps of:
(i) construction of a mitochondrial expression vector,
(ii) reversible induction of megamitochondria, and
(iii) transfection of the megamitochondria with the mitochondrial expression vector by means of a physical transfection method.

The mitochondrial expression vector of the present invention may have at least two constituents to be able to fulfil its function: exogenous DNA, i.e. a gene to be expressed and/or a selection marker, and a mitochondrial promotor region. In a preferred embodiment still other constituents are available, such as a selection marker and/or reporter genes, signal sequences and/or transcription termination sequences (TSS), replication origins and/or a safety mechanism.

Prior to the introduction of these mitochondrial expression vectors into the mitochondria it is necessary to reversibly induce the mitochondria into megamitochondria. The reversible induction of the megamitochondria is preferably conducted by acetification or acidification of the culture medium which may comprise the mammalian cells. The culture medium is acidified either by the addition or by the creation of pH-lowering substances, preferably of acids or salts thereof, preferably lactic acid, acetic acid or sodium acetate, preferably acetic acid or sodium acetate, wherein the pH in the culture medium is preferably adjusted to between 5.3 and 6.7 to produce an acidic culture medium. The concentrations of the acids or the salts thereof are in the acidified culture medium preferably between 5 and 100 mM, wherein the preferred concentration for acetic acid is between 30 and 35 mM and for sodium acetate is between 50 and 60 mM. For the reversible induction of the megamitochondria according to the present invention, the mammalian cells are incubated in the acidified medium preferably for between 20 min and 2 days, wherein the induction of the megamitochondria is reversible due to the exchange of the acidified culture medium with a culture medium which has a pH≥7.0, preferably a pH≥7.4, and no additional pH-lowering substances.

The reversible induction of the megamitochondria or the selection of the acid/salt used for the acidification is conducted on the basis of the physical transfection method, wherein the physical transfection method is selected from the group consisting of the bombardment of the cells with DNA-coated microparticles in a gene gun, the transfection by means of magnetic particles and the microinjection, wherein the microinjection is the most preferred method since the microinjection uses very large mitochondria (preferably >3 μm) and thus it can be visually monitored whether the mitochondria were actually transfected or penetrated. A specific embodiment of the present invention induces, prior to the bombardment of the mammalian cells with DNA-coated gold particles in a gene gun or prior to the transfection by means of magnetic particles, the megamitochondria by acidification of the culture medium by means of lactic acid and, prior to the microinjection of the mammalian cells, the megamitochondria by the acidification of the culture medium by means of the addition of sodium acetate or acetic acid.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE FIGURES

The following detailed description, given by way of example, but not intended to limit the invention solely to the specific embodiments described, may best be understood in conjunction with the accompanying drawings.

FIG. 26A-B shows the optimized sequence mtoGFP, wherein the upper line each indicates the RNA sequences (U instead of T) (SEQ ID NO: 7) and the lower line lists the resulting amino acid sequence (SEQ ID NO: 8) after a translation in the mitochondria (*=stop). The modified tryptophan codon Trp58 is in bold-face and underlined.

DETAILED DESCRIPTION OF THE INVENTION

Figure 1:
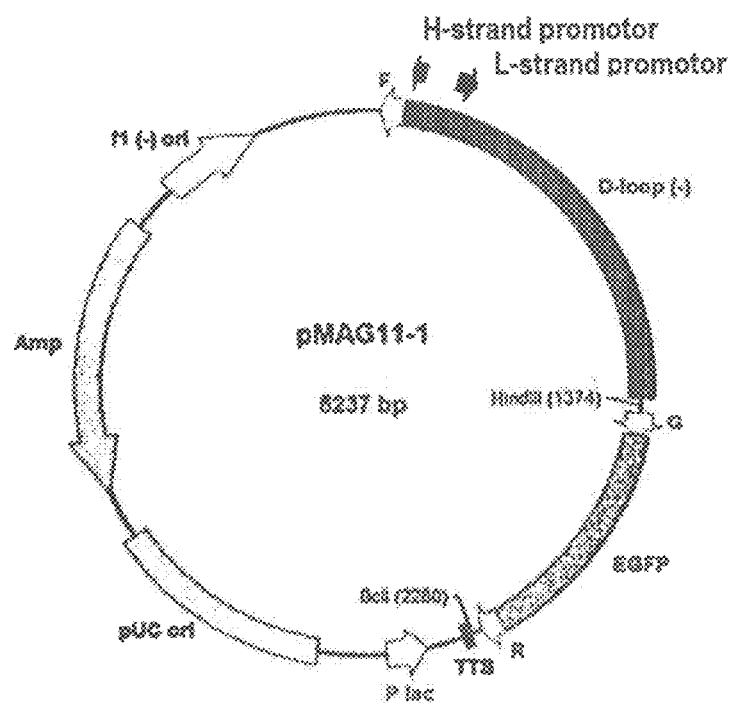
FIG. 1 shows the vector map of pMAG11-1.

The present invention provides physical transfection methods by means of which exogenous DNA which is integrated in a mitochondrial expression vector is introduced in vivo or in vitro into the mitochondria of mammalian cells or cells, wherein the mitochondria are induced into megamitochondria prior to the application of the physical transfection method. These transfection methods can be used e.g. to treat mitochondrial diseases by somatic gene therapy, wherein the moiety of mutated mitochondrial DNA (mtDNA) is either forced below the threshold value necessary for manifesting clinical symptoms or the mutated mtDNA is completely removed.

The human mitochondrial DNA or mtDNA is an annular double helix of 16 595 base pairs (bp) and has a supercoiled conformation. The sequence has been fully clarified since 1981 (Anderson, S. et al., Nature, 1981, 290: 457-465) and comprises the sequence for 37 genes. Thirteen genes thereof code for polypeptides which are integral constituents of four of the five respiratory chain complexes. Seven of these genes (ND1 to ND6 and ND4L) code for subunits of the NADH ubiquinone oxidoreductase (complex I) and a (CYTB) for cytochrome b, a constituent of the ubiquinol cytochrome c-oxidoreductase (complex III). Furthermore, three genes (COX1 to COX3) for subunits of the cytochrome c-oxidase (complex IV) and two genes (TP6/8) for subunits of the ATP synthase (complex V) are available on the mitochondrial DNA. In addition, the genome also contains two ribosomal RNAs (rRNAs) and 22 genes for transfer RNAs (tRNAs) which are essential for the mitochondrial translation system.

The two DNA strands of the DNA double helix are divided into a heavy strand (H-strand, heavy) and a light strand (L-strand, light) due to their different purine and pyrimidine contents (Berk, A. J. and D. A. Clayton, J. Mol. Biol., 1974, 86: 801-824). The majority of the information is coded with the genes for two rRNAs, 14 tRNAs and twelve polypeptides on the H-strand, while the L-strand only carries one protein gene and eight tRNA genes (Anderson, S. et al., Nature, 1981, 290: 457-465).

In contrast to the nuclear genome, the mitochondrial genome has an extremely compact structure. In addition to the lack of introns, the genes in part border directly on one another without any non-coding sequence or they even overlap, and therefore some of the termination codons are not completed until the transcription by polyadenylation of the mRNAs has been carried out. Here, the protein and rRNA-encoding genes are usually flanked by a tRNA gene. All in all, there are only three non-coding regions, the largest of which comprises 1123 bp and is referred to as displacement loop (D-loop) (Anderson, S. et al., Nature, 1981, 290: 457-465). The designation D-loop describes one of the main conformations of the mitochondrial DNA which has a triple DNA structure at this location. It contains a short, newly synthesized H-strand molecule (7S DNA) which enters into base pairings with the L-strand (Tapper, D. P. and D. A. Clayton, J. Biol. Chem., 1981, 256: 5109-5115). Furthermore, the D-loop represents a region which is responsible for the regulation of the replication and transcription of the mitochondrial genome. It includes the starting point of the replication or the replication origin (ori) of the H-strand ($O_H$), conserved sequence blocks (CSB I-III), termination-associated sequences (TAS) and the promotors for the transcription with the designation HSP1 (heavy strand promotor 1, H1 promotor) and LSP (light strand promotor) and HSP2 (heavy strand promotor 2, H2 promotor), which differ as regards their transcription rates, wherein the H1 promotor has a transcription rate which is 20 to 30 times higher than that of the H2 promotor and is approximately twice as intense as the L-strand promotor (King, M. P. and G. Attardi, J. Biol. Chem., 1993, 268: 10228-10237).

Therefore, the "mitochondrial expression vector" or "expression vector" or the "mitochondrial expression plasmid" or "expression plasmid" of the present invention must have at least two constituents to fulfil its function: exogenous DNA, i.e. a gene to be expressed, and a mitochondrial promoter region. A preferred embodiment still contains other constituents, such as a selection marker and/or reporter genes, signal sequences and/or transcription termination sequences (TSS), replication origins and/or a safety mechanism.

In a preferred embodiment, the term "mitochondrial expression vector" or "expression vector" or "mitochondrial expression plasmid" or "expression plasmid" refers to a complete mitochondrial genome or a derivative thereof.

The "exogenous DNA" or the "gene to be expressed" represents an essential constituent of the expression vector of the present invention, which is integrated into the expression vector to enable e.g. a somatic gene therapy of the above mentioned mitochondrial diseases. In this case, the gene to be expressed is a "therapeutic gene". The term "therapeutic gene" is an intact replicative and transcription-active gene to compete with the mutated genes; an intact gene to exchange the mutated genes by means of recombination; genes which code for antisense oligonucleotides to inhibit the replication of the mutated mtDNA.

The "mutated genes" of the present invention may comprise e.g. the mutated forms of genes of the mtDNA, the genes for the pyruvate dehydrogenase, the pyruvate carboxylase, for the proteins of the citric acid cycle, the respiratory chain complexes I to IV or the ATP transport proteins or genes which code for proteins or protein complexes which are involved in the regulation of the mitochondrial replication, transcription or the translation, which may comprise e.g. the genes for transcription factors (TFAM, TFB1M, TFB2M), the mitochondrial RNA polymerase (POLRMT), mitochondrial termination factors (mTERF1-mTERF4), the mitochondrial DNA polymerase γ (POLG), the mitochondrial single-stranded binding protein mtSSB (single strand binding), the helicase TWINKLE, types I and II mitochondrial topoisomerases, the mitochondrial peptidases MIP (mitochondrial intermediate peptidase) and MPP (mitochondrial processing peptidase), the mitochondrial heat shock protein mtHSP70 (mitochondrial heat shock protein).

The changes in the mutated genes of the mtDNA of the present invention are caused by gene mutations which are selected from the group consisting of point mutations by substitution, deletion mutations by deletion, insertion mutations by insertion and duplication mutations by duplication, in particular from deletion mutations or point mutations. The deletions in the mutated genes have a size between 1.0 and 10 kb, in particular between 1.3 and 8.0 kb, are usually located between the two mitochondrial replication origins $O_H$ and $O_L$ and are usually flanked by short repeat sequences. In contrast to deletion mutations, the point mutations of the mutated genes of the mtDNA of the present invention are found throughout the mtDNA, e.g. in protein genes, tRNA or rRNA genes, in particular in the tRNA genes. While point mutations in protein genes only relate to individual constituents of the respiratory chain, the entire mitochondrial protein biosynthesis and thus all mitochondrially encoded respiratory chain subunits are impaired by point mutations in the tRNA and rRNA genes.

The "intact genes" of the present invention thus may comprise the corresponding non-mutated forms of the above listed genes which code for the pyruvate dehydrogenase, the pyruvate carboxylase, for the proteins of the citric acid cycle, the respiratory chain complexes I to IV or the ATP transport proteins or for proteins or protein complexes which are involved in the regulation of the mitochondrial replication, transcription or the translation.

Furthermore, a "selection marker" or marker and/or reporter gene can also be integrated into the expression vector in addition to or in place of the gene to be expressed to enable the use of the mitochondrial expression vector in fundamental research, for example. The "selection marker" allows the distinction between transfected cells and non-transfected cells, in particular living cells. In this connection, the selection marker may comprise the coding sequence or the gene which codes for a fluorescent protein or for a reporter enzyme, or an antibiotic resistance gene.

Preferred fluorescent proteins are e.g. the green fluorescent protein (GFP), the blue fluorescent protein (BFP), the cyan fluorescent protein (CFP) or the yellow fluorescent protein (YFP) or derivatives thereof, wherein the derivatives are selected from the group consisting of the 25 kDa enhanced GFP (EGFP), derivatives of the blue fluorescent protein (e.g. EBFP, EBFP2, azurite or mKalama1), derivatives of the cyan fluorescent protein (e.g. ECFP, cerulean or CyPet) and derivatives of the yellow fluorescent protein (e.g. citrin, venus or YPet), wherein EGFP is the most preferred derivative.

Preferred reporter enzymes and/or genes which code for a reporter enzyme are: e.g. the LacZ gene from *Escherichia coli*, codes for a β-galactosidase (β-Gal); the phoA gene from *Escherichia coli*, codes for an alkaline phosphatase (AP); the gusA gene from *Escherichia coli*, codes for a β-glucuronidase (GUS) (formerly known as uidA gene); the cat gene, codes for a chloramphenicol acetyltransferase (CAT); the luciferase gene from *Photinus pyralis* and *Renilla reniformis*, codes for the bioluminescence enzyme luciferase, preferably for the firefly luciferase.

Preferred antibiotic resistance genes are e.g. the ampicillin resistance gene ampR (also known under the designation of blaTEM1), the tetracycline resistance gene, the kanamycin resistance gene, neomycin resistance gene or the chloramphenicol resistance gene ($Cam^R$), wherein the chloramphenicol resistance gene is the most preferred one.

In a preferred embodiment of the present invention, more than one selection marker, e.g. two selection markers, e.g. the sequence coding for EGFP and the chloramphenicol resistance gene, are integrated into the expression vector of the present invention. In a further preferred embodiment of the present invention, the selection marker/s is/are integrated into the expression vector of the present invention together with the gene to be expressed.

In a specific embodiment of the invention, "flanking tRNAs" are fused to both sides of the respective integrated gene, e.g. of the gene to be expressed or the selection marker, to ensure the correct processing of its own gene constructs. After the transcription, these tRNAs mark the processing sites by the formation of their classical cloverleaf structures as "recognition sites" for the processing enzymes by adopting their classical cloverleaf structure as a secondary structure and are then cut out of the transcript by means of restriction cleavage. As a result, the RNAs of the flanked gene regions are released and can then be further modified, e.g. polyadenylation of the mRNAs and rRNAs at the 3'-end by a mitochondrial poly(A) polymerase. The "flanking tRNAs" of the present invention can be all mitochondrial and nuclear tRNAs, preferably the tRNAs or tRNA pairs for glycine and arginine, leucine and valine, aspartate and lysine.

Along with the gene to be expressed and/or the selection marker, the expression vector of the present invention includes another essential constituent: a mitochondrial promotor region. According to the present invention, the term "mitochondrial promotor region" is understood to mean the D-loop of the mitochondrial genome, which contains the sequences important for the transcription initiation. The three independent mitochondrial promotors for the L- and H-strands: HSP1, HSP2 and/or LSP, the starting point of replication or replication origin of the H-strand ($O_H$), conserved sequence blocks (CSB I-III) and termination-associated sequences (TAS) belong thereto.

The mitochondrial promoter region enables the regulated expression of a gene which was integrated into the expression vector of the present invention, wherein RNA polymerases are the enzymes which catalyze the synthesis of RNA in the transcription of the DNA. Mammalian mtDNA is usually transcribed by a "mitochondrial RNA polymerase" (POLRMT or mtRNApol) which has a great sequence similarity with respect to RNA polymerases from bacteriophages (Masters, B. S. et al., Cell, 1987, 51: 89-99). However, the mitochondrial RNA polymerase gene does not belong to the essential constituents which are to be integrated into the expression vector of the present invention, and therefore the already existing mitochondrial RNA polymerase of the transfected mitochondrion is usually used on the basis of the present invention. However, since POLRMT does not have the ability to independently interact with the promotor DNA so as to initiate the transcription, but requires additional trans-active factors or transcription factors for this purpose, such as the mitochondrial transcription factors A (TFAM, mtTFA), B1 (TFB1M) or B2 (TFB2M), the transcription factors of the transfected mitochondrion are also used on the basis of the present invention in addition to the mitochondrial RNA polymerase of the transfected mitochondrion. These transcription factors bind to the mitochondrial DNA in the vicinity of the promotors, thus enabling the binding of POLRMT which can then begin with the transcription.

In another preferred embodiment of the present invention, it is possible to use along with the mitochondrial RNA polymer even another RNA polymerase to enhance the expression rate e.g. of the gene to be expressed and/or the selection marker, e.g. the highly processive RNA polymerase from the bacteriophage 17 ("T7-RNA polymerase"), the RNA polymerase from bacteriophage T3 ("T3 RNA polymerase") and the RNA polymer from bacteriophage SP6 ("SP6 RNA polymerase"). The gene which codes for the T7 RNA polymerase has to be integrated into the expression vector in this embodiment and to be controlled by the mitochondrial promoter. In order to use the transcription enhancement by the T7 RNA polymerase, the gene to be expressed should still be provided with the T7 promotor in this further preferred embodiment, wherein said promotor can be integrated into the expression vector along with the H- and L-strand promotors. Thus, the T7 RNA polymerase is preferably under the control of the mitochondrial promotors, wherein the gene to be expressed and/or the selection marker are produced by the highly processive T7 RNA polymerase.

In a preferred embodiment, a "signal sequence" or "transcription termination sequence" (TTS) is present in the expression vector in the case of another promotor along with the H- and L-strand promotors, e.g. in the case of the integrated T7 promotor, wherein said sequence prevents the T7 promotor-controlled expression e.g. of the gene to be expressed and/or of the selection marker from being impeded by the mitochondrial transcription processes. The TTS of the present invention is preferably located behind the sequence region of the gene to be expressed and/or the selection marker to stop the transcription. In a preferred embodiment of the present invention, one of the flanking tRNAs represents the TTS, preferably the flanking tRNA for leucine which stops the transcription starting from the mitochondrial promotor, e.g. HSP1, so as to enhance the expression of the gene to be expressed and/or the selection marker, for example.

Another enhancement of the expression according to the present invention can be achieved by enabling a proliferation or replication of the expression vector within the mitochondria since then, after a cell division, the expression vector can be passed on to the two daughter cells, which permits a permanent expression. The mtDNA is duplicated by means of a replication machinery of its own, wherein a model assumed in the prior art describes that the mitochondrial replication proceeds asymmetrically from two replication origins (e.g. Shadel, G. S. and D. A. Clayton, Annu. Rev. Biochem., 1997, 66: 409-435).

In the asymmetric model, the replication of the H-strand starts at $O_H$, which is located downstream of the LSP. The primer required for the initiation is formed by the transcription starting from the LSP. The resulting RNA fragment remains bound to the DNA via the conserved sequence blocks (CSB I-III). Together with the displaced H-strand, this RNA/DNA hybrid forms a stable triple-stranded structure, which is referred to as an R-loop. The RNA strand is cleaved by an endonuclease activity at certain sites in the $O_H$ region and can then serve as a primer for the DNA synthesis of the H-strand by the mitochondrial DNA polymerase γ (POLG). The replication of the H-strand stops in most cases in the region of the termination-associated sequences (TAS, 700 bp downstream of the $O_H$). The so-called 7S DNA is formed by the termination process and yields, together with the two strands of the mtDNA, the characteristic triple-stranded structure of the D-loop. However, if the H-strand synthesis is continued, it reaches the $O_L$ after ⅔ of the elongation so as to start the replication of the L-strand in opposite (asymmetrical) direction. The displaced single-stranded DNA at $O_L$ forms a stem-loop structure which results in the recruitment of a possible mitochondrial primase. The latter synthesizes the RNA primer for the replication of the L-strand in the thymidine-rich region of the loop. The transition between RNA synthesis and DNA synthesis is conducted in the region of a pentanucleotide sequence at the base of the secondary structure. If the two strands are replicated, the RNA primers are removed, gaps are filled and ligated and superhelical coils are introduced into the closed circular mtDNA molecules (e.g. Shadel, G. S. and D. A. Clayton, Annu. Rev. Biochem., 1997, 66: 409-435).

Thus, the expression vectors of the present invention, which may comprise the replication origin for the H-strand that is integrated into the mitochondrial promoter region, have the drawback that they are not replicated in the mitochondria, and therefore the expression vector is not passed on to the two daughter cells after a cell division, thus making a permanent expression impossible. Therefore, the replication origin for the L-strand is additionally integrated into the expression vector in a specific embodiment of the present invention, preferably behind the gene to be expressed and/or the selection marker, to avoid the above drawbacks, thus enhancing the expression.

Another mechanism can be introduced into the expression vector of the present invention to prevent the expression e.g. of the gene to be expressed and/or the selection marker after a possible integration into the nuclear genome. For this purpose, e.g. the gene to be expressed and/or the selection marker can be modified in such a way that it is/they are functional after the translation in the mitochondria while a translation in the cytosol creates a non-functional protein. In this connection, "safety mechanisms" are incorporated in a preferred embodiment and are based on the fact that the mtDNA has some differences as regards the codon use in comparison with the nuclear genome.

The translation can also be improved by the use of "codon usage"-optimized genes. For example, a nuclear stop codon, preferably TGA, is integrated into the mitochondrial expression vector, e.g. in the gene to be expressed and/or in the selection marker, in this preferred embodiment, which codes, however, for tryptophan in the mitochondria. Thus, a stop is initiated in a translation e.g. of the gene to be expressed and/or the selection marker in the cytosol, and the protein is obtained in a non-active form.

Therefore, the "mitochondrial expression vector" or "expression vector" of the present invention has at least the two constituents: exogenous DNA, i.e. a gene to be expressed and/or a selection marker, and a mitochondrial promotor region. Only preferred embodiments contain even further constituents, such as further selection markers, signal sequences and/or transcription-termination sequences (TTS), replication origins and/or a safety mechanism. Before the exogenous DNA, which is integrated into the mitochondrial expression vector of the present invention, is introduced into the mitochondria of mammalian cells by means of a physical transfection method, the mitochondria are reversibly induced into megamitochondria beforehand since it is difficult to transfect mitochondria due to their small thickness of 0.5-1 µm.

Mitochondria which are considerably larger than normal mitochondria, as a result of which they can be seen under a light microscope without staining, are referred to as "megamitochondria" or "giant mitochondria" according to the present invention. They distinguish themselves particularly in that they are swollen (PCT/EP2009/004454), thus preferably having a diameter of ≥2 µm, or of 2-10 µm, preferably of 2, 3, 4, 5, 6, 7, 8, 9 or 10 µm, most preferably of 4-10 µm or of 4, 5, 6, 7 or 10 µm.

The megamitochondria are reversibly induced prior to the physical transfection of the mitochondria, wherein according to the present invention the megamitochondria are reversibly induced either by the administration of active substances and/or chemicals into the culture medium, preferably valinomycin (Malka, F. et al., EMBO Rep., 2005, 6: 853-859), chloramphenicol (Albring, M. et al., *Naturwissenschaften*, 1975, 62: 43-44), cuprizone (Suzuki, K., Science, 1969, 163: 81-82) or $H_2O_2$ or hydrazine (Teranishi, M. et al., J. Electron. Microsc., (Tokyo), 1999, 48: 637-651), more preferably valinomycin, or by the incubation of the cells in an acidic culture medium, wherein the culture medium is made sour or acidified by the addition or creation of pH-lowering substances, e.g. acids or the salts thereof (PCT/EP2009/004454), preferably by the addition or creation of lactic acid, lactate, acetic acid and/or sodium acetate or mixtures thereof.

According to the present invention, the term "culture medium" or "nutrient medium" refers to the substrate which serves as a culture for the cells. The culture media suitable for the present invention are e.g. the Iscove's medium, RPMI medium, Dulbecco's MEM medium, MEM medium, F12 medium, Dulbecco's modified Eagle's medium (DMEM) or Eagle's minimum essential medium (EMEM). These media can be enriched with additives, such as with fetal calf serum, bromodeoxyuridine, pyruvate, uridine, Earle's salts, L-glutamine, sodium bicarbonate or non-essential amino acids.

"Valinomycin" is a $K^+$-selective cycloside peptide which acts as an ionophore and uncouples the oxidative phosphorylation. For the reversible induction of megamitochondria, the cells are to be incubated prior to the physical transfection of the mitochondria in culture medium with 1-20 µM valinomycin for 1-5 h, preferably in culture medium with 10 µM valinomycin for 1, 2 or 4 h.

Along with the reversible induction of the megamitochondria by the addition of chemicals, the incubation of the cells in acidic culture medium is also a possibility of causing the mitochondria to swell. The culture medium has to be acidified for this purpose by the addition or the creation of pH-lowering substances, e.g. acids or salts thereof, to a pH of between 5.3 and 6.7, preferably between 5.7 and 6.3 or between 6.4 and 6.5.

The acidification by means of pH-lowering substances can be conducted, on the one hand, by the addition of lactic acid or the salts thereof, e.g. lactate, and therefore the final concentration of lactic acid or the salt thereof in the culture medium is preferably between 5 and 100 mM, preferably between 40 and 70 mM. This produces a pH in the culture medium between 5.3 and 7.0, preferably between 5.3 and 6.7, preferably between 5.7 and 6.3 or between 6.4 and 6.5, most preferably a pH of 6.3 (see PCT/EP2009/004454).

Further acids which can be used as pH-lowering substances for acidifying the culture medium on the basis of the present invention may comprise acetic acid and the salts thereof, for example. Acetic acid or the salts thereof are added in such a way that the final concentration thereof in the culture medium is between 5 and 100 mM, preferably between 25 and 40 mM, more preferably between 30 and 35 mM. This produces a pH in the culture medium of between 5.3 and 7.0, preferably from 5.7 to 7.0, preferably between 6.3 and 7.0, most preferably a pH of 6.3.

With respect to the acetic acid, in particular the sodium salt thereof, i.e. sodium acetate, can be used as a pH-lowering substance, wherein the addition thereof is made in such a way that the final concentration is between 5 and 100 mM, preferably between 45 and 65 mM, preferably 45, 50, 55, 60 or 65 mM, most preferably between 50 or 60 mM. This produces a pH in the culture medium between 5.3 and 7.0, preferably between 5.7 and 7.0, preferably between 6.3 and 7.0, most preferably a pH of 6.3.

Furthermore, the acidification can also be effected by metabolic products which result from the cultivation of the cells in the culture medium without changing the medium, i.e. the acidification can be conducted by "creating pH-lowering substances" in the culture medium, e.g. lactate, which is formed during the decomposition of sugars due to lactic acid fermentation as a metabolic intermediate product in a concentration between 15 and 50 g/l, preferably between 25 and 30 g/l, and is thus produced by the mammalian cells per se and has a pH between 6.3 and 7.0, preferably between 6.7 and 6.8.

The mammalian cells are incubated for the reversible induction of the megamitochondria according to the present invention in an acidified medium, preferably for between 10 min and 5 days, preferably for between 20 min and 2 days, more preferably for 20 min, 60 min and 2 days. The incubation is preferably carried out at 37° C., a relative humidity of 95% and exposure to 5% $CO_2$ gas.

The term "mammalian cells" or "cells" refers to cells of mammalian cell lines according to the present invention, wherein "mammalian cell lines" may comprise the cell lines 143B.TK$^-$, 143B.TK$^-$ +pEGFP-Mito, 143B.TK$^-$ +pEGFP-OMP, 143B.TK$^-$K7 and Hela296-1. At the time of the reversible induction of the megamitochondria, the mammalian cell cultures had a cell density between 1 and $5 \times 10^5$ cells per 35 mm dish, preferably of $3 \times 10^5$ cells per 35 mm dish. When converted, this is approximately $1-5 \times 10^4$ cells per cm². In another embodiment, the term "mammalian cells" or "cells" may comprise according to the present invention "rho⁰ cells" or "ρ⁰ cells" (see PCT/EP2008/010586) which are used for transfection experiments according to the invention by means of mtDNA, where complete mitochondrial genomes or parts/derivatives thereof are to be incorporated.

The induction of the megamitochondria, which is carried out according to the present invention, distinguishes itself in that it is reversible, wherein the term "reversible" or "reversibility" is understood to mean the reversion, i.e. the megamitochondria produced by induction can return to the state prior to their induction without modifications. For this purpose, the culture medium enriched or acidified with active substances is exchanged in each case with a culture medium which is either not enriched with active substances, e.g. with pH-lowering substances, or not acidified, i.e. preferably has a pH of ≥7.0, preferably a pH≥7.4.

The method for the induction of the megamitochondria or the selection of the active substance used for the enrichment or the acid or salt used for the acidification is conducted on the basis of the transfection method. According to the present invention, the term "transfection" is understood to mean the introduction of foreign DNA into eukaryotic cells, thus allowing the cell to express foreign or heterologous genes after the DNA incorporation. A distinction is made between two types of transfection: In the "transient transfection", a vector is introduced into the host cell to achieve a transiently strong expression of a heterologous gene. However, this expression is rapidly reduced with the dilution of the vector with every cell division. An integration of the vector into the genome of the cell by illegitimate recombination is very rare, and therefore the dilution fails to proceed. In a "stable transfection", a long-term gene expression is aimed at as a result of a permanent incorporation of the vector DNA into the host genome. However, the precondition is that a selectable gene is cotransfected. If retroviral expression vectors are used, a stable integration of the vector DNA is ensured.

According to the present invention, a physical transfection method should be used, wherein the physical transfection method is selected from the group consisting of the bombardment of the cells with DNA-coated microparticles in a gene gun, the transfection by means of magnetic particles and the microinjection.

The cells are bombarded with DNA-coated microparticles, preferably gold or tungsten particles, according to the present invention in a gene gun which is here a biolistic, i.e. strictly mechanical, method serving for shooting DNA by means of particles into cells. In this connection, the DNA is applied onto the surface of the particles which are then shot at high pressure onto the mammalian cell. At the destination, i.e. in the mitochondria, the DNA is then released and can be expressed. On the basis of the present invention, specific parameters were set to achieve a transfection rate of up to 8%. The microparticles (tungsten or gold particles, preferably gold particles) have a diameter between 0.2 and 5 µm, preferably from 0.6 to 2.5 µm, preferably of 0.6, 1.0, 1.2 or 1.6 µm, more preferably of 0.6 µm, wherein between 0.1 and 5 µg, preferably between 0.5 and 2 µg, preferably 1 µg of the mitochondrial expression plasmid, and 0.05 to 2.5 µg, preferably 0.1 to 1.0 µg, preferably 0.5 µg, particles are to be used for each transfection batch.

According to the present invention, the bombardment of the cells with DNA-coated particles has to be carried out at chamber pressures between 5 and 50 in Hg, preferably between 15 and 27 in Hg, preferably at 15, 20, 25 and 27 in Hg, more preferably at ≥25 in Hg, most preferably at 27 in Hg partial vacuum or in a vacuum, using 100-3000 psi, preferably 1350-2000 psi, preferably 1350, 1550, 1800 or 2000 psi, more preferably 1800 psi rupture disks; and/or at one of the insertion levels A-D of the gene gun, wherein A is the uppermost and D the lowermost insertion level, preferably at the second uppermost insertion level (level B) or the second lowermost level (level C), preferably at the second lowermost level (level C) of the gene gun, wherein the cells should be cultured for the bombardment in plastic culture dishes having a diameter of 35-150 mm, preferably of 35, 60, 100 or 150 mm, preferably of 35. The DNA is applied to the microparticles according to the present invention by precipitating the DNA in the presence of the particles preferably by neutral salts, preferably by $CaCl_2$, wherein this process can even be enhanced by the addition of 0.05-0.2 M, preferably of 0.1 M, spermidine.

Along with the bombardment of the cells with DNA-coated microparticles in a gene gun, the physical transfection of the megamitochondria can also be conducted by means of magnetic particles. In this method, magnetic particles, preferably magnetic nanoparticles, e.g. MagTag™, are used to transport DNA into the cells, wherein the magnetic particles are coated with DNA, distributed over the cells in the culture medium and drawn into the cells by a magnetic plate where they release the DNA. This method has the advantage that the cell membrane is not influenced by chemical reagents. For this purpose, transfection reagents are used and may comprise the magnetic nanoparticles, e.g. MaTra-A (IBA, Göttingen, Germany).

Another physical transfection method is the transfection by microinjection of DNA where a glass capillary is pushed through the cell membrane through which then different nucleic acids, e.g. the mitochondrial expression vector and/or the mitochondrial expression plasmid, can be introduced into the cell.

For the microinjection according to the present invention, the cells must be seeded onto glass bottom dishes having an integrated raster to be able to subsequently find the injected cells more easily. After the induction of megamitochondria, the mammalian cells are to be injected to a micromanipulator. For this purpose, the injection capillary is filled with 10-500 ng/µl, preferably with 50-350 ng/µl, DNA solution containing the mitochondrial expression plasmid, are to be connected to the apparatus and to be advanced to the mammalian cells to be injected by means of the micromanipulator. The actual injection is carried out directly axially into the megamitochondria at an injection pressure of 50-150 hPa, preferably 90-120 hPa, an injection time of 0.1-0.2 s and/or a holding pressure of 40-50 hPa.

The microinjection is the most preferred physical transfection method of the present invention since the microinjection uses very large mitochondria (preferably >3 µm), and therefore it is possible to follow visually whether the mitochondria were actually transfected or penetrated.

Prior to the bombardment of mammalian cells with DNA-coated gold particles in a gene gun or prior to the transfection using magnetic particles, the megamitochondria are induced by means of acidification of the culture medium using lactic acid and prior to the microinjection of the mammalian cells, the megamitochondria are induced by acidification of the culture medium by the addition of sodium acetate or acetic acid according to a specific embodiment of the present invention.

Therefore, the subject matter of the present invention also relates to a method for introducing exogenous DNA into mitochondria of mammalian cells, which may comprise the steps of:
(i) constructing a mitochondrial expression vector,
(ii) reversibly inducing megamitochondria, and
(iii) transfecting the megamitochondria with the mitochondrial expression vector by means of a physical transfection method.

The following examples serve for illustrating the subject matter of the present invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

Microbiological Methods

Liquid Cultures of Bacteria

Required Material:
LB medium
Antibiotic stock solution
Conduction:

10 ml LB medium, depending on the required amount, were charged in a 50 ml tube or 5 ml in a 15 ml tube for a liquid culture. If required, the necessary antibiotic (table 1) was added for the selection of the desired bacterial strain. The medium was incubated by means of a sterile pipette tip with a picked colony from an agar plate over night at 37° C. while shaking.

TABLE 1

Antibiotic concentrations employed

| Antibiotic | Concentration of the stock solution | Dissolved in | Stock solution/ml medium | Final concentration in the medium |
|---|---|---|---|---|
| Ampicillin | 50 mg/ml | ddH2O | 2-3 µl | 100-150 µg/ml |
| Kanamycin | 10 mg/ml | ddH2O | 5 µl | 50 µg/ml |
| Tetracycline | 5 mg/ml | ethanol | 10 µl | 50 µg/ml |
| chloramphenicol | 34 mg/ml | ethanol | 0.5-5 µl | 17-170 µg/ml |

Example 2

Collection of Mitochondrial DNA from Human Placenta (modified according to Fernandez-Silva, P. et al., Methods Enzymol., 1996, 164, 129-139)

Human mitochondrial DNA can be prepared in relatively large amounts from placenta. This is the simplest way since other human tissues are only accessible with difficulty while placentas occur with every birth. The preparation is mainly based on a differential centrifugation where the mitochondria are purified from nucleus and cell debris and the DNA is subsequently prepared therefrom.

Required Material:
Sucrose-TE buffer (STE)
Sucrose-TE buffer+(STE+)
Sucrose-TE buffer with MgCl$_2$ (STEM)
0.5 M EDTA
5 M NaCl
0.5 M SDS
DNase I (RNase-free)
RNase A (DNase-free)
aseptic gauze
Miracloth
glass homogenizer
Corex glass centrifuge tube
Conduction:

After the collection from the labor room, the placenta was cooled on ice. Thereafter, the placenta was cut into small pieces and the connective tissue and the larger vessels were cut off. The pieces were then washed in STE until almost no more blood escaped. After weighing (usually 300-350 g), the pieces were frozen at −80° C. up to further processing in the form of a thin plate. After starting to thaw for about 1 h at room temperature, the plate was comminuted (by breaking) into small pieces which were then slowly stirred in 1 l STE for 1.5 h until they were fully thawed. Having transferred the pieces in 600 ml new STE, the comminution was carried out in a mixer for 3×20 s at a low speed. After a centrifugation for 15 min at 500×g and 4° C. for removing the cell debris, the supernatants were poured through two layers of mull and stored for subsequent use. The pellets were resuspended in 200 ml STE and again comminuted in a mixer for 3×20 s. After another centrifugation at 500×g and 4° C. for 15 min, the supernatants were poured through the already used mull layers and the pellets were squeezed through two new layers of mull and one layer of MiraCloth to obtain the remaining liquid. The combined supernatants (about 500 ml) were further comminuted in the glass homogenizer by 4-5 strokes at 100 rpm and centrifuged at 4° C. and 1500×g for 15 min. The centrifugation was repeated at least two times with the supernatants until almost no pellet could be seen any more. Then, the mitochondria were centrifuged off the supernatant at 10,800×g and 4° C. for 20 min. The pellet was either used for the production of an in vitro transcription extract or resuspended in 120 ml STEM and pottered in a glass homogenizer with two strokes at 100 rpm. DNase dissolved in STEM was added at a final concentration of 0.1 mg/ml, the samples were distributed over four 50 ml reaction vessels and incubated in a water bath at 37° C. for 30 min. After the inactivation of DNase I by the addition of 7 ml 0.5 M EDTA for each reaction vessel and a subsequent incubation at room temperature for 10 min, the mitochondria were centrifuged off at 4° C. and 15,000×g for 20 min. The pellets were taken up in 80 ml STE+, distributed over two 50 ml reaction vessels and 0.8 ml 5 M NaCl was added each. Then, 0.5 M SDS was added (about 0.5-1 ml) until the mitochondria were lyzed and the solution became clear. Thereafter, the solution of each reaction vessel was admixed with 2.5 mg DNase-free RNase A and incubated in a water bath at 37° C. for 1 h. The samples were combined, distributed over six 50 ml reaction vessels, subjected to a phenol/chloroform extraction, distributed over 16 Corex glass centrifuge tubes and precipitated over night at −20° C. without the addition of sodium acetate. After drying in air, each pellet was taken up in 500 µl ddH$_2$O, combined, dialyzed and precipitated again. The pellet was taken up in 500 µl ddH2O, analyzed by means of gel electrophoresis after a restriction cleavage with PvuII and stored at −20° C. If enough samples (5-8 pieces) had been purified, they were combined, admixed with 50 μg/ml DNase-free RNase A and incubated in a water bath at 37° C. for 1 h. Then, purification by means of CsCl gradient centrifugation was carried out. After the dialysis, the DNA was precipitated, taken up in 100 μl ddH$_2$O and analyzed by means of gel electrophoresis after a restriction cleavage with PvuII and by means of a Southern Blot. The DNA was stored at −20° C. up to its further use. The mitochondria purified from human placenta were taken up in two volumes of MS buffer and then centrifuged off at 4° C. and 13,000×g for 10 min. The pellet was taken up in a volume ML buffer, admixed with 0.5% Tween 20 and 0.5% KCl and incubated on ice for 10 minutes. The lysate was suspended in a glass homogenizer by 10 strokes at 100 rpm and centrifuged at 4° C. and at 13,000×g for 45 min. The clear supernatant (S-13 extract) was carefully removed, aliquoted, frozen in liquid nitrogen and then stored at −80° C. The extract remained active for at least one year.

Example 3

In Vitro Transcription of Mitochondrial Plasmids 3.1. Production of a Mitochondrial In Vitro Transcription Extract (modified according to Fernandez-Silva, P. et al., Methods Enzymol., 1996, 164, 120-139)

In an in vitro transcription, the RNA is synthesized by means of a template DNA in a cell-free system. Since the mitochondria have a transcription system of their own, none of the established transcription systems can be used for the in vitro transcription of mitochondrial genes. However, it is possible by producing a transcription extract from isolated mitochondria to use the transcription with mitochondrial promotors.

Required Material:
Purified mitochondria from placenta
MS buffer (mitochondria suspension buffer)
ML buffer (mitochondria lysis buffer)
Tween 20
5 M KCl
Conduction:

The mitochondria purified from human placenta were taken up in two volumes of MS buffer and then centrifuged off at 4° C. and 13,000×g for 10 min. The pellet was taken up in one volume of ML buffer, admixed with 0.5% Tween 20 and 0.5% KCl and incubated on ice for 10 minutes. The lysate was suspended in a glass homogenizer by 10 strokes at 100 rpm and centrifuged at 4° C. and 13,000×g for 45 min. The clear supernatant (S-13 extract) was carefully removed, aliquoted, frozen in liquid nitrogen and then stored at −80° C. The extract remained active for at least one year.

3.2. In Vitro Transcription

Before it is used in an in vitro transcription, the template DNA must be linearized by a restriction endonuclease downstream of the promotor and of the fragment to be transcribed. If this is not done, a plurality of different RNAs is obtained on account of the processivity of the RNA polymerases. In order to protect the resulting RNA molecules from possibly existing RNases, it is useful to add an RNase inhibitor.

Required Material:
Linearized template DNA
RiboLock™ RNase inhibitor
rNTP-Mix, 25 mM each
DEPC-H$_2$O
S-13 in vitro transcription extract
2× transcription buffer
Transcription stop buffer
Conduction:

For the in vitro transcription, the following batch was joined by pipetting with a reaction volume of 100 μl on ice:
x μl template DNA (2 μg)
2.5 μl RiboLock™ RNase inhibitor (100 U)
4 μl rNTP-Mix
ad 35 μl DEPC-H$_2$O
15 μl S13 in vitro transcription extract
50 μl 2× transcription buffer The batch was incubated at 30° C. for 45 min, and the reaction was then stopped by the addition of 200 μl transcription stop buffer.

3.3 Purification of the RNA from the In Vitro Transcription Extract

In order to be able to separate RNA from the reaction batch which has a high protein content, the batch is subjected to a phenol/chloroform extraction. By the use of phenol having a pH of 4.5-5, the RNA is enriched in the aqueous phase while the DNA rather collects in the interphase, and therefore a DNA contamination in the RNA eluate is reduced. The solvent, i.e. phenol, troubles subsequent enzymatic reactions and therefore has to be removed carefully by a plurality of shaking steps using chloroform.

Required Material:
Phenol pH 4.5-5
Phenol/chloroform/Isoamyl alcohol, 25:24:1 (v/v/v)
Chloroform/isoamyl alcohol, 24:1 (v/v)
Chloroform
DEPC-H$_2$O
Conduction:

The RNA solution was shaken out using successively one volume of phenol, one volume of phenol/chloroform/isoamyl alcohol and one volume of chloroform/isoamyl alcohol. In between, centrifugations at 14,000×g were carried out in each case at room temperature until the phases were fully separated, and thereafter the upper aqueous phase which contained the RNA was transferred to a new reaction vessel. In order to make sure that the RNA solution has lost all the phenol, the chloroform/Isoamyl alcohol extraction was carried out up to five times (an interphase should not be visible any longer). Chloroform instead of chloroform/Isoamyl alcohol was used in the last step. Then, the nucleic acids were precipitated by means of ethanol. The pellet was taken up in 25 μl DEPC-H$_2$O.

Example 4

Cell Culture 4.1. Cultivation of Cells

The cultivation of cells was carried out by observing all safety measures under low-germ conditions. The cell growth was checked by means of an inverted microscope with phase contrast device. As a general rule, the recommended values for the employed culture vessels, which are indicated in table 2, applied.

TABLE 2

Recommended values for culturing cells

| Vessel | Area ($cm^2$) | Cell density during seeding | Cell density in the case of confluence | Growth medium (ml) | PBS (ml) | Trypsin (ml) |
|---|---|---|---|---|---|---|
| Bottles | | | | | | |
| TC 25 | 25 | $0.7 \times 10^6$ | $2.8 \times 10^6$ | 5 | 2 | 1 |
| TC 80 | 75 | $2.0 \times 10^6$ | $8.0 \times 10^6$ | 15 | 6 | 2 |
| Dishes | | | | | | |
| 35 mm | 8 | $0.3 \times 10^6$ | $1.2 \times 10^6$ | 2.5 | 2 | 0.5 |
| 60 mm | 21 | $0.7 \times 10^6$ | $3.2 \times 10^6$ | 5 | 4 | 1 |
| 100 mm | 55 | $2.0 \times 10^6$ | $8.0 \times 10^6$ | 10 | 8 | 2 |
| 150 mm | 148 | $5.0 \times 10^6$ | $2.1 \times 10^7$ | 20 | 15 | 4 |

In order to detect possible contaminations with mycoplasms, controls by means of the VenorGeM® *Mycoplasma* Detection Kit were carried out at regular intervals according to the instructions of the manufacturer. The cells were cultured as a matter of routine at 37° C. and a relative humidity of 95% in the $CO_2$ gas-flushed incubator and passaged depending on the growth properties every two to four days.

4.2. Transfection of Eukaryotic Cells 4.2.1. Transfection with the Transfection Reagent METAFECTENE® PRO METAFECTENE® PRO is a polycationic transfection reagent which is available in combination with a neutral colipid in liposomal form. DNA enters the cells by initially complexing the DNA to be transfected in compact structures and incorporating it endocytotically into the cells. The release of the nucleic acids from the endosomes is accomplished inside the cells by buffer properties of the complexing agents, which increase the osmotic pressure in the endosome in such a way that the membrane breaks open. This process is supported by the properties of the cationic lipids which destabilize the endosomes as a result of the acidification by means of protons (repulsive membrane acidolysis). Since the DNA is taken into the cell nucleus predominantly during the disruption of the nuclear membrane (mitosis), the transfection should at best be carried out with strongly proliferating cells.
Required Material:
METAFECTENE® PRO (Biotex, Martinsried, Germany)
Conduction:
The transfections were carried out in accordance with the supplied instruction (as per July 2005). In order to prevent a possible adsorption of the reagents to the vessel walls, only polystyrene vessels were used for the transfection.

4.2.2. Transfection with the FuGENE® HD Transfection Reagent

FuGENE® HD is a non-liposome-based transfection reagent and forms a complex with the DNA to be transfected and then transports the latter into the cell. As in the case of METAFECTENE® PRO, a transfection with FuGENE® HD should only be carried out with strongly proliferating cells.
Required Material:
FuGENE® HD (Roche, Mannheim, Germany)
Conduction:
The transfections were carried out in accordance with the supplied instruction (as per October 2005).

4.2.3. Transfection with the Transfection Reagent MATra-A

This transfection reagent uses magnetic nanoparticles (MagTag™) to introduce the desired DNA into the cells. In the first step, the DNA is adhered to the nanoparticles which then penetrate the cells by magnetic attraction (by means of a magnetic plate which is placed underneath the culture dish) where they can release the DNA on their surface. This method has the advantage that the cell membrane is not influenced by chemical reagents and also provides good results in the case of cells which can only be transfected poorly by means of liposome-based transfection reagents.
Required Material:
MAtra-A (IBA, Gottingen, Germany)
Magnetic plate
Conduction:
The transfections were carried out in accordance with the supplied instruction (as per July 2006).

Example 5

Selection of Transfected Cells by Antibiotics

A selection of positive clones is a must for a stable transfection. A pure culture of cells that contains the desired construct is only achieved in this way.
Required Material:
Selection antibiotic
Conduction:
The selection of the transfected cells was guaranteed by antibiotics, for which the corresponding resistance genes were available on the respective constructs to ensure a survival of the positive clones. It was initially determined in connection with each antibiotic from what concentration all non-transfected cells of a culture dish died or stopped growing. For this purpose, the various cell lines were seeded in the corresponding culture media and incubated with the respective antibiotic at various concentrations. The selective medium was changed every other day and the cells were observed over a total of eight days. Cells which were incubated in the standard medium without antibiotic served as a negative control. The required amount of antibiotic for the selection after a transfection was determined by the concentration at which all cells in the culture dish had died after four to five days. The selection was started between 24 and 48 h after the transfection.

Example 6

Selection of $\rho^0$ Cells Transfected with mtDNA

Only one metabolic test is available for the selection of $\rho^0$ cells transfected with mtDNA. In this test, the dependence of the $\rho^0$ cells on uridine and pyruvate is used to select the cells repopulated with mtDNA. In contrast to the $\rho^0$ cells, these cells can also grow without the addition of uridine and pyruvate, thus forming clones on the culture plate while the $\rho^0$ cells die after some time.
Required Material:
$\rho^0$ selection medium Conduction:

The cells to be investigated were removed enzymatically from the cell culture dish and newly seeded onto a 150 mm culture dish with selection medium. The medium was exchanged every other day for approximately one week and thereafter every four days. If no clones could be detected after three to four weeks, the culture dish was discarded.

Example 7

Production of Dialyzed FCS

Low-molecular constituents of FCS can gently be removed by dialysis. This is above all important for the use of the FCS in the selection medium for $\rho^0$ cells since here possibly available uridine and pyruvate molecules are a disturbing factor.

Required Material:
Dialysis tube, MWCO 3.5 kDa
Locking clamps
FCS dialysis buffer
Sterile filter
Conduction:

One end of the dialysis tube was initially folded twice and then closed with a locking clamp. Thereafter, the FCS was filled into the dialysis tube which was carefully closed in the same way as done at the other end. In this connection, care was taken that no air bubbles were trapped in the tube interior. The tube was attached in a 10 l plastic bucket with 8 l FCS dialysis buffer in such a way that it did not contact the magnetic stir bar. The dialysis was carried out at 4° C., wherein the dialysis buffer was exchanged after two and another four hours. Then, the dialysis was continued over night. The next morning, the FCS was removed from the tube, sterile filtrated and stored in aliquoted fashion at −20° C.

Example 8

Staining of Mitochondria with MitoTracker® Dyes

By means of the MitoTracker® dyes it is possible to selectively stain mitochondria in living cells. The red fluorescent MitoTracker® dyes are derivatives of either tetramethylrosamine or X-rosamine and contain a thiol-reactive chloromethyl unit which is likely responsible for their association with the mitochondria.

Required Material:
MitoTracker® Red CMXRos or MitoTracker® Deep Red FM from Invitrogen, Karlsruhe, Germany
Conduction:

MitoTracker® Red CMXRos or MitoTracker® Deep Red FM was added to the medium of living cells at a dilution of 1:1,000 and incubated in an incubator at 37° C. for 30 min. Then, the medium was exchanged and another incubation of 15 to 120 minutes was carried out in the incubator at 37° C. before the cells were studied under a microscope and/or fixed.

Example 9

Induction of Megamitochondria 9.1. Induction Via Acidification of the Medium by Means of Lactic Acid The acidification of the culture medium by means of lactic acid is a possibility for inducing the swelling of the mitochondria.

Required Material:
2 M lactic acid
Conduction:

The culture medium was admixed with 2 M lactic acid up to a pH of 6.4-6.5 and then incubated in a culture dish in an incubator at 5% $CO_2$ and 37° C. for several hours. Thereafter, the pH was checked again and, if required, adjusted again with 2 M lactic acid. The cells were incubated with the acidified culture medium in the incubator for one to several hours before they were used for the corresponding experiments.

9.2. Induction Via the Addition of Valinomycin

Valinomycin is a $K^+$-selective cyclodepsipeptide which acts as an ionophore and uncouples the oxidative phosphorylation. In this connection, the mitochondria swell within some few hours.

Required Material:
Valinomycin stock solution (10 mM in DMSO)
Conduction:

The induction was carried out by the addition of the valinomycin stock solution to the culture medium at a ratio of 1:1,000.

9.3 Induction via acidification of the medium by means of sodium acetate

Required Material:
3 M sodium acetate, pH 5.2
Conduction:

The sodium acetate was pre-incubated at the desired final concentration together with the culture medium in a 60 mm culture dish at room temperature for 20 min and then placed on the seeded cells.

9.4. Induction Via Acidification of the Medium by Means of Acetic Acid

Required Material:
Acetic acid
Conduction:

The acetic acid was pre-incubated at the desired final concentration together with the culture medium in a 60 mm culture dish at room temperature for 20 min and then placed on the seeded cells.

Example 10

Particle Bombardment with the Gene Gun

The here used device was the PDS-1000/He system of the Bio-Rad company.

10.1. Preparation of the Device

At the beginning of each use, the device and part of the subsequently used materials have to be prepared. In this connection, the entire conduit system and the pressure piston are flushed with helium. Furthermore, the macrocarriers are prepared for subsequent use.

Required Material:
Helium pressure cylinder
Macrocarrier
Stainless steel holder for macrocarrier
Rupture disk (corresponding to the applied pressure)
Stopping screen Conduction:

In order to rinse the system with helium, the pressure piston was closed with a rupture disk as described in the instruction and a stopping screen was inserted in the holder provided for this purpose (uppermost level). After a chamber vacuum was applied, a pressure was built up until the disk ruptured. Then, the chamber was aerated and the pressure piston was immediately closed again with a new rupture disk. The macrocarriers were inserted in the associated stainless steel holders. In doing so, care had to be taken that the macrocarriers were precisely fitted into the groove intended for this purpose.

10.2. Preparation of the Gold Particles

The gold particles have to be prepared before they are coated with DNA. The pretreatment shall ensure that the particles are sterile and free from other contaminants and that they are not available as conglomerates, if possible.

Required Material:
Gold particles (0.6 μm, 1.0 μm or 1.6 μm diameter)
70% ethanol p.a. (v/v)
50% glycerol (v/v), sterile
Sterile water
Conduction:

30 mg of the gold particles were initially weighed in a 1.5 ml reaction vessel. Then, 1 ml 70% ethanol was added, mixed on the vortexer at maximum speed for 4-5 min and incubated at room temperature for 15 min. The gold particles were centrifuged off for 5 s (by means of the short spin button) and the supernatant was discarded. Thereafter, the gold particles were mixed in 1 ml sterile water for 1 min on the vortexer and incubated at room temperature for 3 min. Then, the gold particles were centrifuged off, and, after discarding the supernatant, this wash step was repeated two more times. Finally, the gold particles were taken up in 500 μl 50% glycerol (final concentration: 60 mg/ml) and separated by ultrasound for 3×10 s. Storage was in the refrigerator at 4° C.

10.3. Coating the Gold Particles with DNA

In order for the DNA to be introduced into the cell with the gold particles, the DNA must be first applied onto the particles. This is done by precipitating the DNA in the presence of the particles by $CaCl_2$. In doing so, the DNA is attached to the surface of the particles and can then be prepared therewith. This process can even be enhanced by the addition of spermidine.

Required Material:
Gold particles (60 mg/ml, from 3.5.1.2)
DNA solution (333 ng/μl)
2.5 M $CaCl_2$
0.1 M spermidine
70% ethanol p.a. (v/v)
100% ethanol p.a.
Conduction:

The prepared gold particles from 10.2 were again separated by ultrasound and 60 μl was transferred into a new 1.5 ml reaction vessel. In order to ensure a uniform distribution of the DNA on the gold particles, 20 μl DNA solution, 75 μl 2.5 M $CaCl_2$ and 30 μl 0.1 M spermidine were added under continuous mixing on the vortexer (average speed) at an interval of 10 s each. After another 3 min on the vortexer, the then coated gold particles were allowed to stand at room temperature for 5-10 min in order for them to sediment at the bottom of the reaction vessel. After a centrifugation for 2-3 s (in no case longer! by means of the short spin button), the supernatant was discarded and the gold particles were immediately resuspended with a pipette in 180 μl 70% ethanol. After the gold particles could sediment at room temperature for 5-10 min, another centrifugation was carried out for 2-3 s. This wash step was repeated two more times with 100% ethanol, the particles were taken up in 60 μl 100% ethanol and then immediately used for the bombardment of eukaryotic cells.

10.4 Particle Bombardment of Human Cells

For the bombardment with microparticles, human cell lines should be cultured in plastic culture dishes with a diameter of 35 mm. Since the maximum bombarded area corresponds approximately to the size of a 35 mm dish, the use of larger dishes does is not accompanied by any advantages.

Required Material:

DNA-coated gold particles

Macrocarrier in the stainless steel holders

Rupture disks (corresponding to the applied pressure, usually 1800 psi)

Stopping screens

Human cells on 35 mm dishes (30-70% confluence, depending on the application and the cell line)

Culture medium (possibly with antibiotic)

Conduction:

The DNA-coated gold particles were resuspended carefully once again with a pipette and 10 μl each were dripped on the middle of the prepared macrocarriers. After drying (about 10 min), a stainless steel holder with a macrocarrier and a stopping screen was inserted according to the operating instructions in the holder provided for this purpose (gold particles on the bottom side). The culture medium on the cells was almost completely removed and the culture dish was immediately inserted in the apparatus (second level from below). After the evacuation (depending on the experiment, usually 25-27 in Hg) of the chamber, the bombardment was carried out at a pressure corresponding to the inserted rupture disk. After the immediate aeration of the chamber, the culture dish was provided with 2 ml culture medium and then the dish was placed in the incubator. This procedure was repeated with the remaining culture dishes (a total of six items). The success of the particle bombardment was checked under the microscope after 24-48 h.

Example 11

Construction of Mitochondrial Expression Vectors

The mitochondrial expression vectors were designated according to the following pattern:

pMAGx-y (MAG: mitochondrial artificial genome)

Here x corresponds to the group (starting with 11) which focuses on the constituents of the mitochondrial DNA, which are used in the respective vector, and the employed promotor (table 3) and y is the consecutive number in the respective group.

TABLE 3

Arrangement of the constructed mitochondrial expression vectors in groups

| Vector group | Mitochondrial constituents | Employed promoter |
| --- | --- | --- |
| 11 | D-loop + TTS | L-strand |
| 12 | D-loop + TTS | H-strand |
| 13 | D-loop + TTS + L-strand replication origin | H-strand |
| 14 | D-loop + L-strand replication origin + 16S rRNA (Cam$^R$) | H-strand |
| 15 | D-loop 16S rRNA (Cam$^R$) | H-strand |
| 16 | D-loop | H-strand |
| 17 | D-loop + L-strand replication origin | H-strand |

11.1 pMAG11-1

In this vector, EGFP was introduced as a reporter gene to obtain a detection which can be reproduced in simple and rapid fashion regarding a successful transfection (FIG. 1). The flanking tRNAs were selected in such a way that they were available in the same orientation as in the mitochondrial DNA. In this case, the tRNAs were used for glycine and arginine, which usually flank the ND3 gene that codes for a subunit of the NADH ubiquinone oxdoreductase. In this connection, attention had to be paid to the fact that the stop codon of the ND3 gene is incomplete, i.e. that it only consists of a T which is completed by the polyadenylation into TAA (Ojala, D. et al., Nature, 1981, 290, 470-474).

Figure 2A:
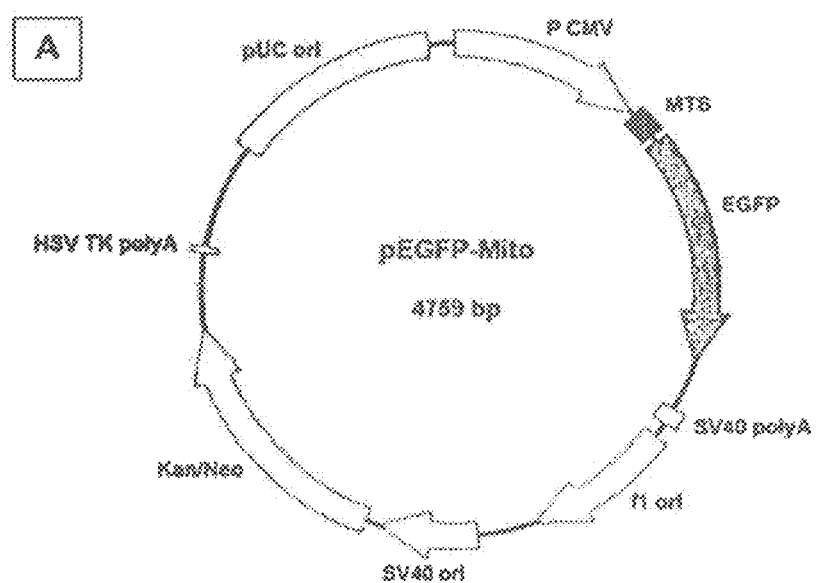
FIG. 2A shows the vector map of pEGFP-Mito.
Figure 3:
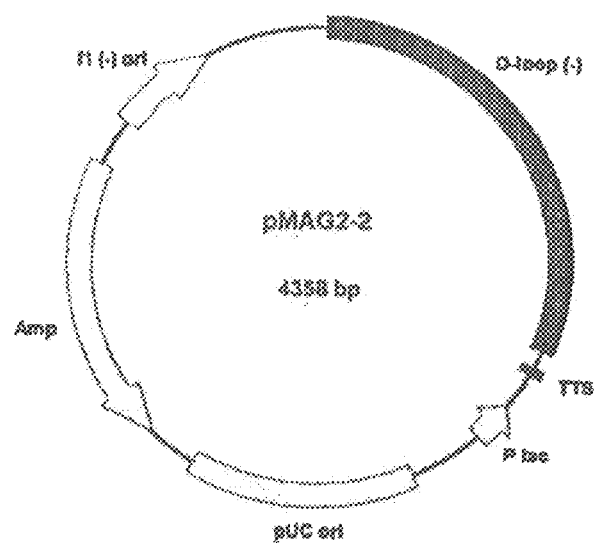
FIG. 3 shows the vector map of pMAG2-2.

The two tRNAs were composed in each case of four oligonucleotides (GFP link 1-4 or GFP link 5-8) which were able to bind to one another in an annealing reaction. At the two ends, overhangs having a length of four nucleotides were formed to be able to bind to the EGFP gene and the vector. The EGFP gene was amplified from the vector pEGFP-Mito which carries the gene for EGFP, at the C-terminus of which the signal peptide of the human cytochrome-c oxidase subunit 8 was fused (FIG. 2A), with the primers EGFP-001-FOR (4) [5'-CTTTTGGTCTCAATGATGGTGAGCAAGGG-3' (SEQ ID NO: 1)] and EGFP-716-REV (4) [5'-GTTAGTGGTCTCTATTTGTACAGCTCGTCC-3'(SEQ ID NO: 2)]. Here, BsaI cleavage sites were attached to the ends to obtain overhangs compatible with the tRNAs. This enzyme does not cleave the DNA in its recognition sequence but displaced by a nucleotide in the 3'-direction. This results in a 5'overhang which comprises four bases and which could be defined by the sequence of the employed PCR primer. Then, the tRNAs were ligated together with the BsaI-treated PCR product into the BclI and HindIII cleaved vector pMAG2-2 (FIG. 3) which like the vector pMAG2-1 contains the complete D-loop of the human mitochondrial DNA and additionally carries the transcription termination sequence (TTS). The resulting vector was sequenced and was given the name pMAG11-1.

11.2. pMAG11-2

Figure 4:
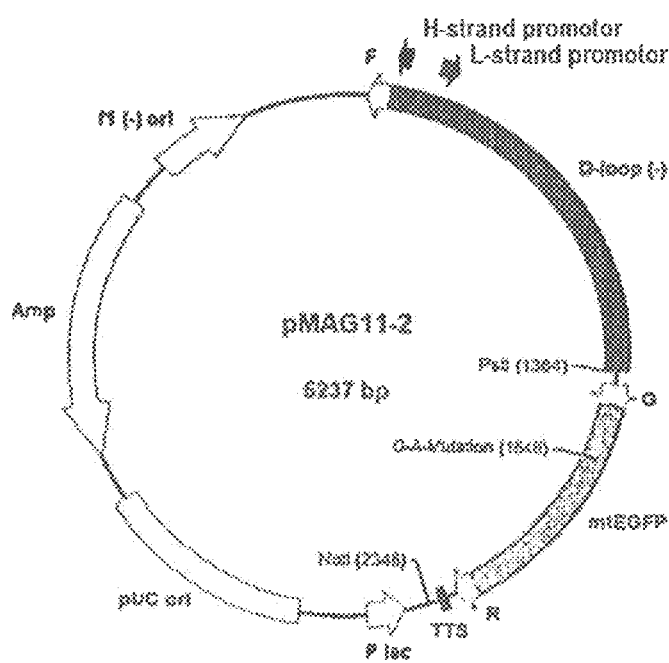
FIG. 4 shows the vector map of pMAG11-2.

An additional safety mechanism was incorporated into the pMAG11-2 vector to prevent an expression of the EGFP gene after a possible integration into the nuclear genome. In the mutagenesis PCR of the pMAG11-1 vector, the primers EGFP-156-FOR [5'-CAAGCTGCCCGTGCCCTGAC-CCACCCTCGTGACCAC-3'(SEQ ID NO: 3)] and EGFP-191-REV [5'-GTGGTCACGAGGGTGGGTCA-GGGCACGGGCAGCTTG-3'(SEQ ID NO: 4)] was used to change the tryptophane at site 58 (Trp58) of EGFP from TGG into TGA. After the sequencing, the correct mitochondrial EGFP (mtEGFP) and some surrounding regions were cut out with the restriction endonucleases PstI and NotI and ligated into the likewise treated pMAG11-1 vector. The newly resulting plasmid had the name pMAG11-2 (FIG. 4).

Alternatively to the here listed mtEGFP, a GFP fully adapted to the codon usage of the mitochondria (mtoGFP) can also be used in this vector and the following vectors. It likewise contains the modification of Trp58 and additionally numerous modifications on a DNA level which, however, have no effects on the remaining amino acid sequence in a translation into mammalian mitochondria. Due to these modifications, however, the translation is optimized into mitochondria and the efficiency of a possible translation (up to the stop codon at the site 58) is reduced in the cytoplasm (FIG. 26).

11.3. pMAG12-1

Figure 5:
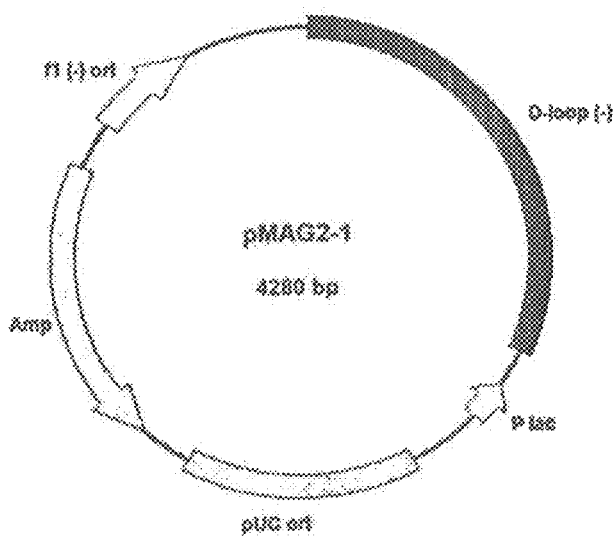
FIG. 5 shows the vector map of pMAG2-1.
Figure 6:
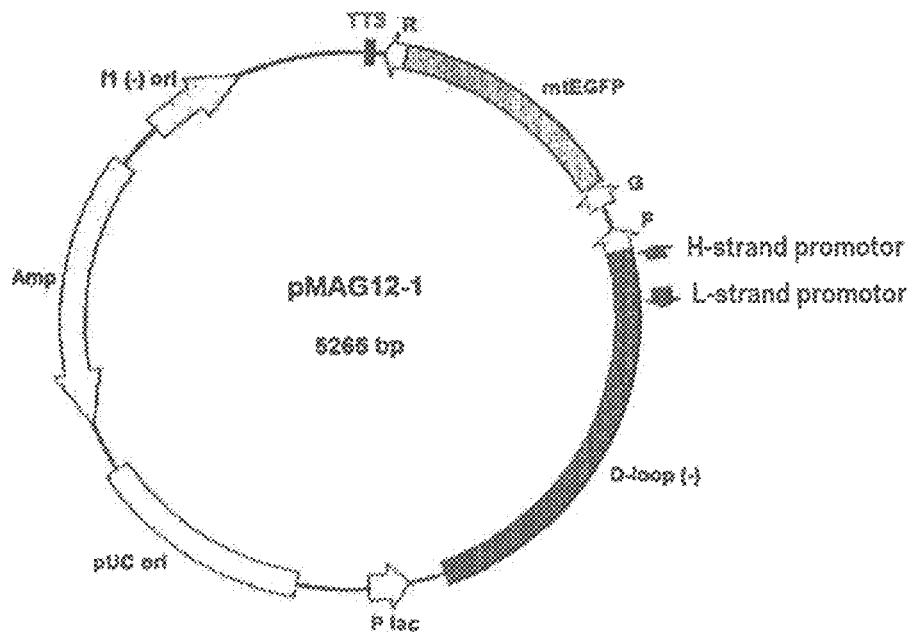
FIG. 6 shows the vector map of pMAG12-1.

In order to optimize the expression of the mtEGFP, the mtEGFP gene including the attached tRNAs and the TTS was cloned in reverse orientation on the other side of the D-loop. For this purpose, the pMAG2-1 plasmid (FIG. 5) was cleaved with XhoI and the pMAG11-2 plasmid with XhoI and NruI. Since the ends were not compatible with one another, all free DNA ends were filled by a treatment with the Klenow fragment. After the subsequent control of the correct orientation of the mtEGFP cassette, the vector was sequenced and was given the name of pMAG12-1 (FIG. 6).

11.4. pMAG13-1

Figure 7:
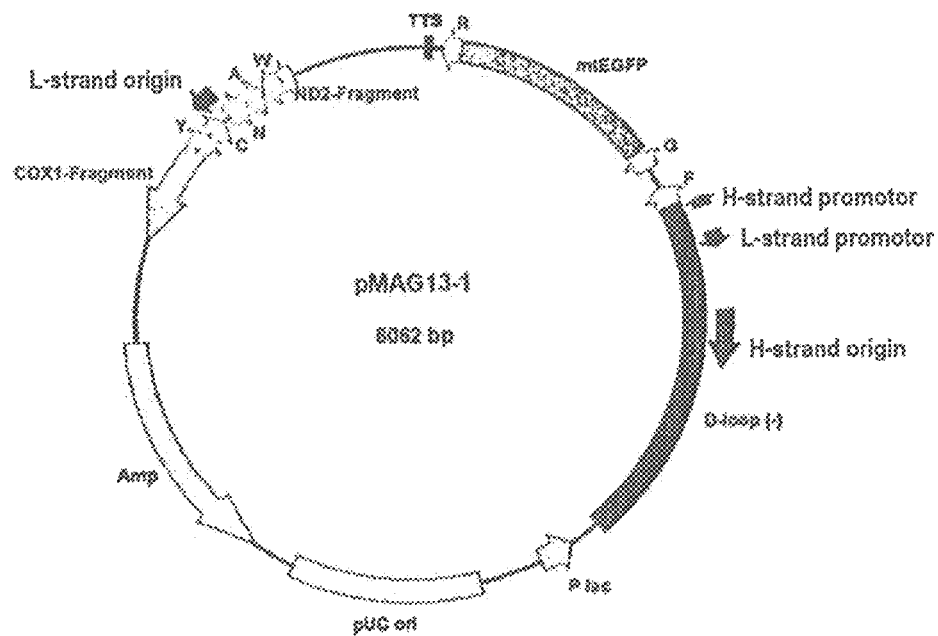
FIG. 7 shows the vector map of pMAG13-1.

Although the pMAG12-1 vector could be replicated in bacteria, it could not be replicated in the mitochondria since it only carried the replication origin for the H-strand which is disposed in the D-loop region. The replication origin for the L-strand is in the mitochondrial DNA, however, in a region which was not available in the constructed pMAG12-1 plasmid. Therefore, a 800 bp long region around the L-strand replication origin of the mitochondrial DNA was integrated into the region of the f1 (−) origin of the pMAG12-1 vector. The region around the replication origin of the L-strand was obtained by amplification with the primers 05465-FOR and 06266-REV from purified placenta mtDNA. The pMAG12-1 vector was linearized by means of the restriction endonuclease DraIII and the overhanging 3'-ends were then removed by means of the Klenow fragment. After the ligation of the PCR product into the vector, the orientation was checked and the vector was sequenced. The resulting vector was given the name pMAG13-1 (FIG. 7).

11.5. pMAG14-1

Figure 8:
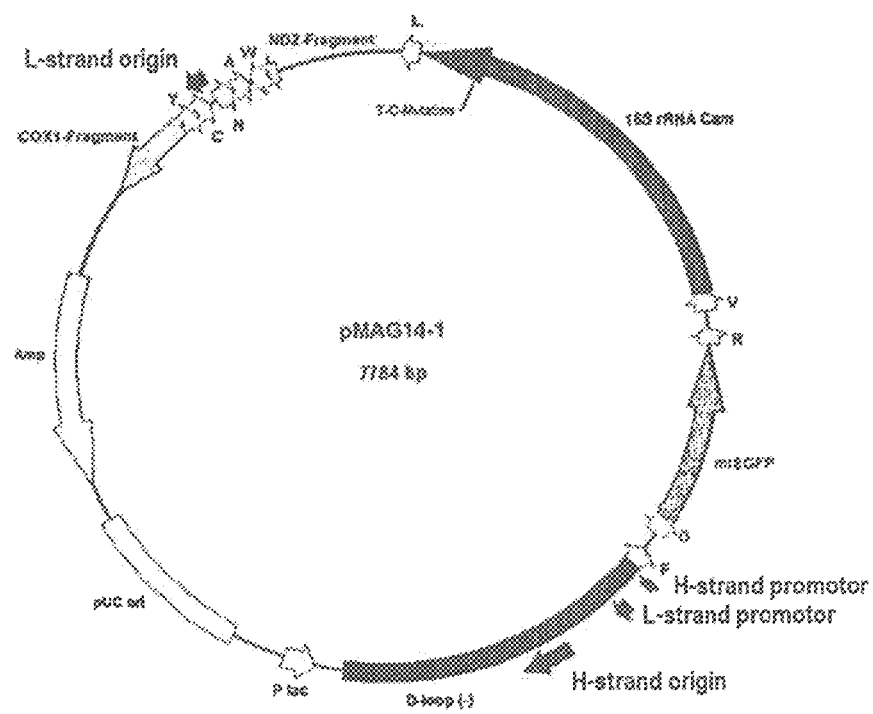
FIG. 8 shows the vector map of pMAG14-1.

The pMG14-1 vector (FIG. 8), a chloramphenicol resistance (Cam$^R$) contained as a second marker gene in addition to mtEGFP which could be used for applying a selection pressure onto the cells. For this purpose, the 16S rRNA gene was amplified together with the flanking tRNAs for valine and leucine from an entire DNA extraction of the cell line HeLa 296-1, with the desired chloramphenicol resistance, by means of the primers 01562-FOR [5'-GCGCTGCAG-TAACATGGTAAGTGTACTGGAAAGTGCAC-3'(SEQ ID NO: 5)] and 03351-REV [5'-AATCTCGAGATTA- GAATGGGTACAATGAG-3' (SEQ ID NO: 6)] and the PCR product was then ligated into the vector. After sequencing the entire insert, the 16S rRNA gene with the tRNAs was cut out by a restriction cleavage using XhoI and BclI. The pMAG13-1 vector was also treated with XhoI and BclI, and therefore the TTS sequence was removed. The 16S rRNA gene could then be ligated with the vector fragment into the new pMAG14-1 vector. In this connection, the previously removed TTS sequence was automatically inserted again since it is located in the leucine tRNA which as a flanking region of the 16S rRNA was cloned as well.

11.6. pMAG14-3

In addition to the replication origin of the L-strand, the pMAG14-3 vector contained the chloramphenicol resistance and the gene which codes for the T7-RNA polymer under the control of the mitochondrial promotor and the mtEGFP gene under the control of the T7 promotor. The mtEGFP gene was integrated into the vector behind the leucine tRNA at the end of the 16S rRNA gene, wherein the tRNA which contains the transcription termination site stops the majority of the mitochondrial transcription processes.

Figure 9:
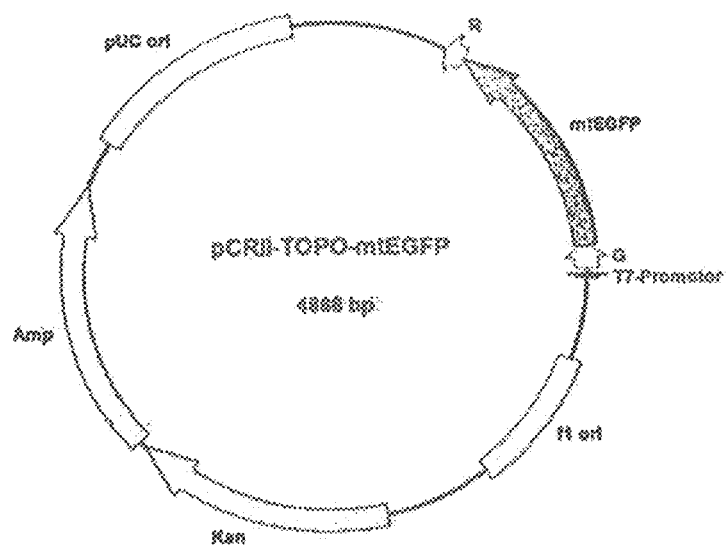
FIG. 9 shows the vector map of pCRII-TOPO-mtEGFP.
Figure 10:
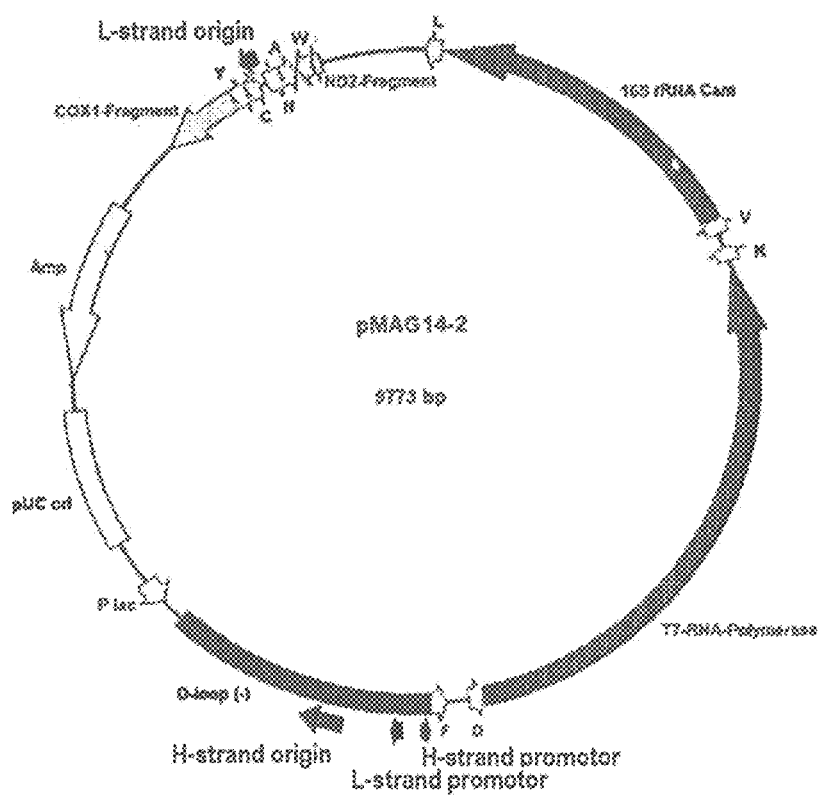
FIG. 10 shows the vector map of pMAG14-2.
Figure 11:
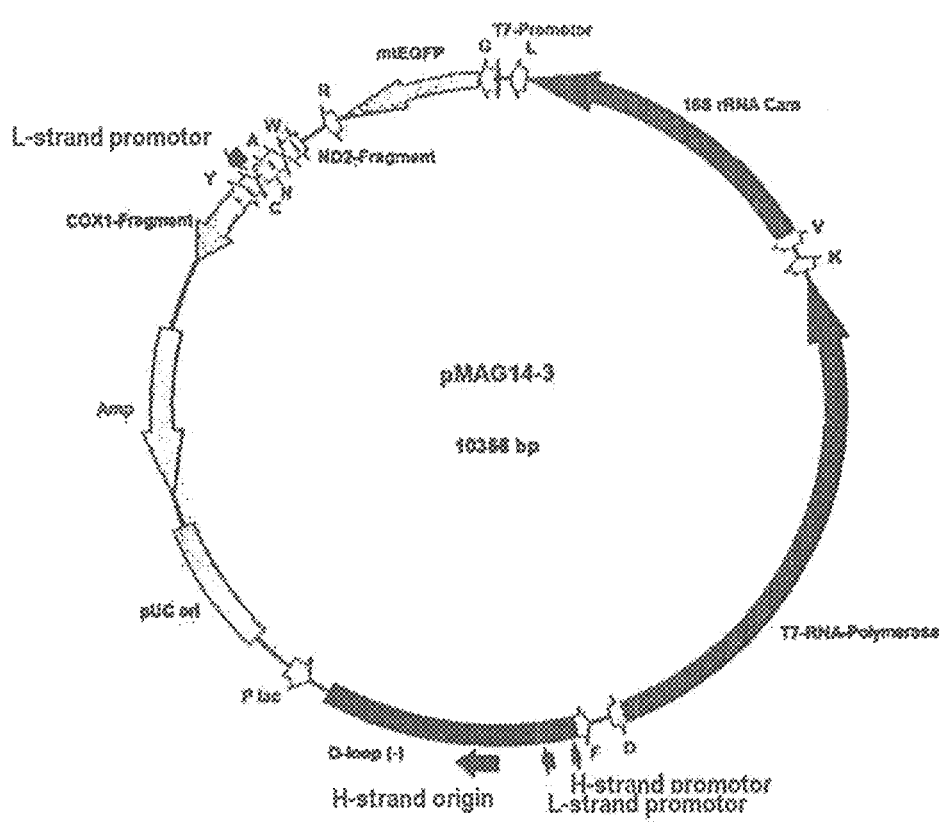
FIG. 11 shows the vector map of pMAG14-3.

For the production of the pMAG14-3 vector, the mtEGFP was cut out of the auxiliary vector pCRII-TOPO-mtEGFP (FIG. 9) by means of the restriction endonucleases PsiI and XhoI in a first step and then ligated with the dephosphorylated 16S rRNA gene which was obtained from the pMAG14-2 vector by XhoI and NdeI via the XhoI overhangs. In the second step, the resulting DNA fragment from 16S rRNA and mtEGFP was ligated into the pMAG14-2 vector treated with PSII and NdeI (FIG. 10). The resulting vector was designated pMAG14-3 (FIG. 11).

Example 12

Results of the Induction of Megamitochondria

Figure 12:
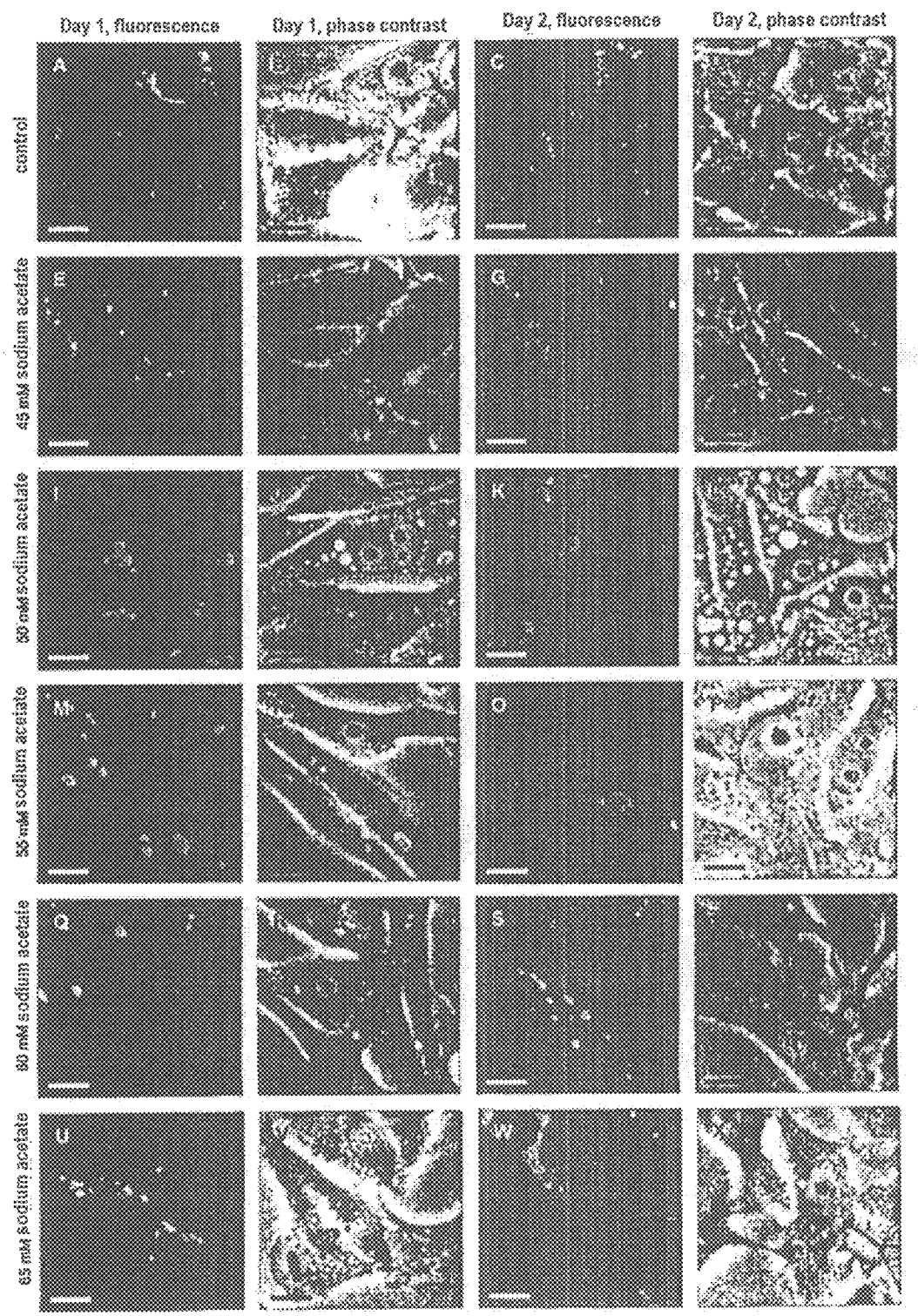
FIG. 12 shows the induction of megamitochondria by sodium acetate, i.e. fluorescence and phase contrast images of megamitochondria induced by sodium acetate in the cell line transfected with pEGFP-Mito, i.e. 143.B.TK⁻. The calibration marks correspond to 10 μm.

12.1 Induction with Sodium Acetate $2 \times 10^5$ to $3 \times 10^5$ cells of the 143B.TK− cell line transfected with the plasmid pEGFP-Mito (FIG. 2A) were seeded onto 35 mm glass bottom dishes and cultured in culture medium at different concentrations (45, 50, 55, 60 and 65 mM) of sodium acetate. On day 1 and day 2 after the addition of the acidified medium, the cells were studied under the microscope for the formation of enlarged mitochondria. While the control cells in sodium acetate-free medium included a network of thin tubular mitochondria after the first day (FIG. 12, A+B), the cells with 45 mM sodium acetate showed first signs of thickened mitochondria (FIG. 12, E+F). With 50 and 55 mM, almost spherical mitochondria having a diameter of up to 4 µm were detectable (FIG. 4, I+J and M+N) while a tubular network was in part also identifiable in the same cells. In the case of further increased concentrations of 60 and 65 mM sodium acetate, the size of the mitochondria decreased again and their shape also changed into partly drop-like swellings of the network (FIG. 12, Q+R and U+V).

On the second day, the culture medium of the control cells was slightly orange and the mitochondria no longer formed a network but almost had the shape of a point (FIG. 12, C+D). Compared to the day before (FIG. 12, G+H, O+P, S+T and W+X) there were almost no changes at 45, 55, 60 and 65 mM, while the mitochondria of the cells in 50 mM sodium acetate were only available as sphere having a size of up to 6 µm (FIG. 12, K+L). It turned out in further test series that the optimum concentration with each new culture medium change and FCS charges had to be redetermined; however, it was usually between 50 and 60 mM sodium acetate.

Figure 2B:
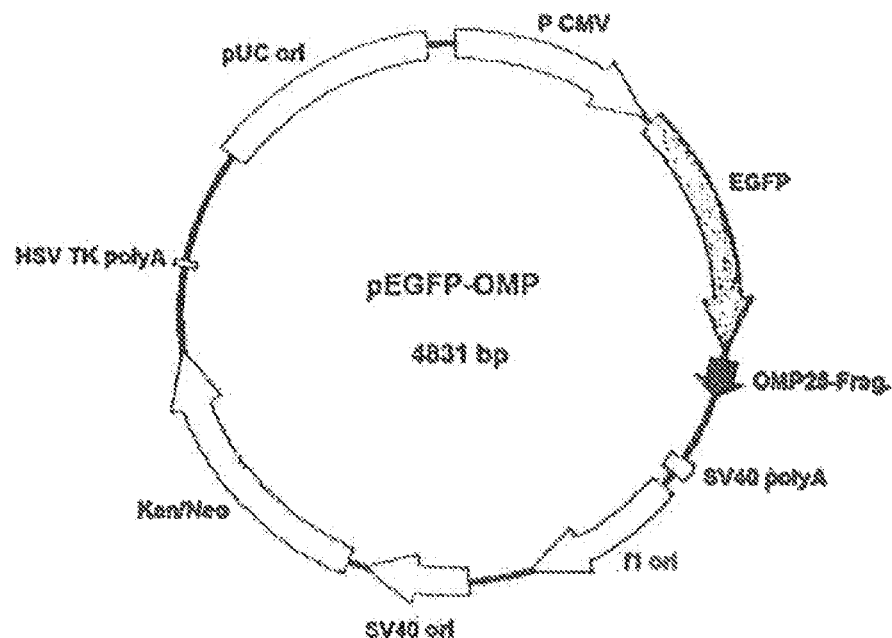
FIG. 2B shows the vector map of pEGFP-OMP which carries the gene for EGFP, to the C-terminus of which the signal peptide of the human cytochrome-c oxidase subunit 8 was fused. As a result, the protein is transported into the matrix of the mitochondria.
Figure 13:
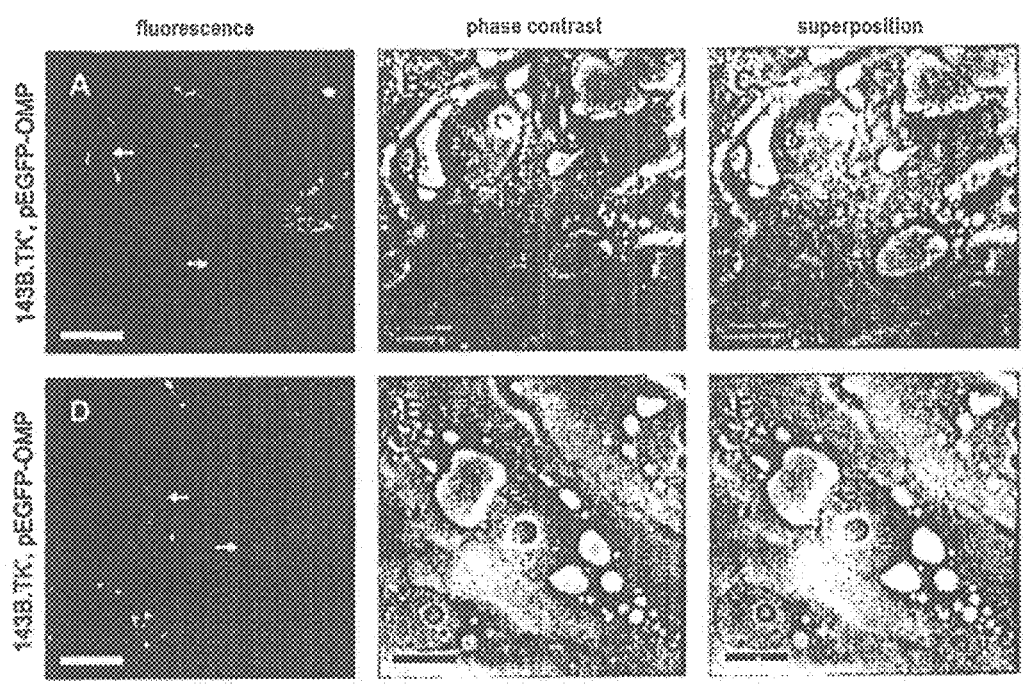
FIG. 13 shows megamitochondria. Images of the cell line stably transfected with pEGFP-OMP, i.e. 143B.TK⁻. Megamitochondria are marked by arrows. A+D: fluorescence images, B+E: phase contrast images, C+F: superposition of A and B or D and E. The calibration marks correspond to 10 μm.

In some experiments, it was possible to achieve swelling of the mitochondria up to almost the size of the cell nucleus. Such giant megamitochondria can be seen in FIG. 13 (arrows at A and D). The here employed cell line was again the 143B.TK− cell line which was stably transfected with pEGFP-OMP (FIG. 2B) and this is why the outer mitochondria membrane thereof was stained.

12.2 Induction with Acetic Acid

In order to induce the megamitochondria with acetic acid, the culture medium was admixed with different concentrations (25-40 mM) of acetic acid and then $2 \times 10^5$ to $3 \times 10^5$ cells of the 143B.TK− cell line transfected with pEGFP-Mito (FIG. 2A) were further cultured therein in 30 mm glass bottom dishes. After one day and another day, an examination was carried out under the microscope.

Figure 14:
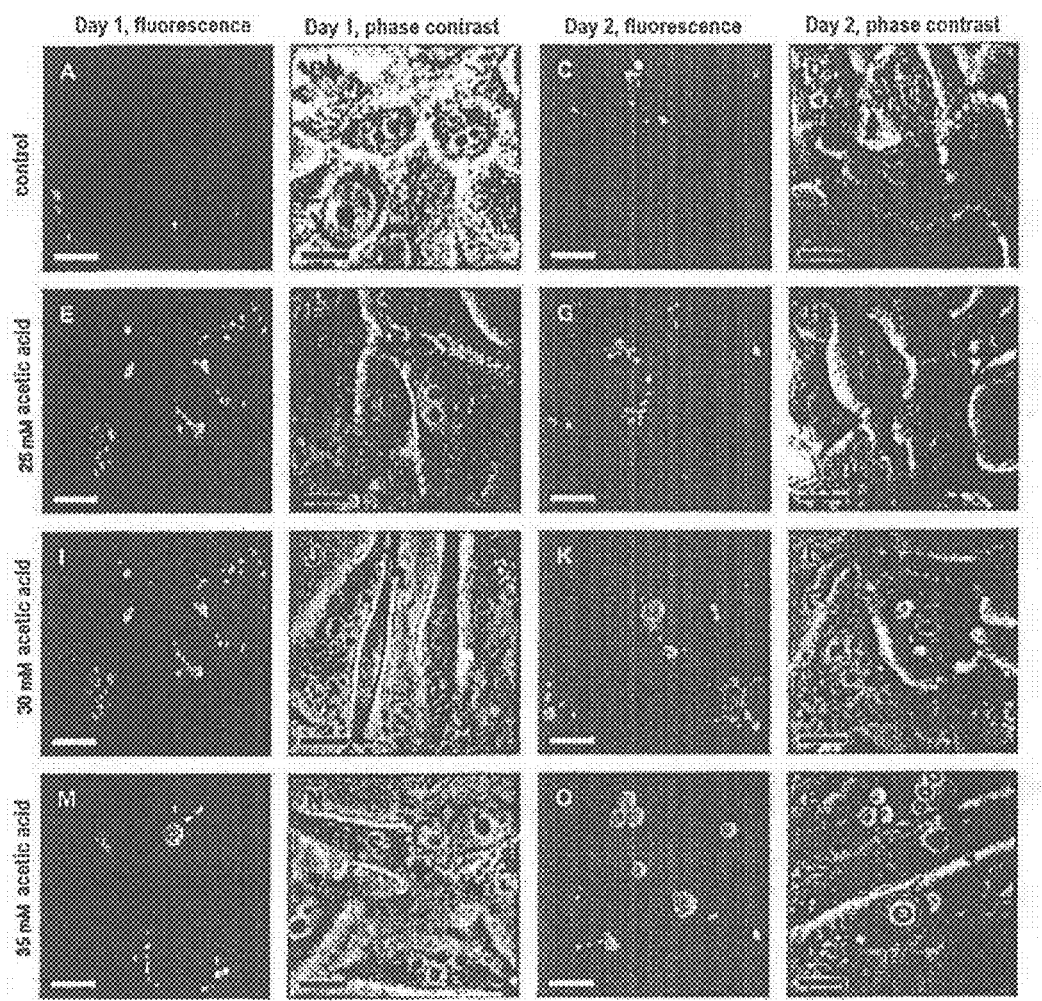
FIG. 14 shows the induction of megamitochondria by acetic acid, i.e. fluorescence and phase contrast images of megamitochondria induced by means of acetic acid in the cell line transfected with pEGFP-Mito, i.e. 143B.TK−. The calibration marks correspond to 10 μm.

The cells in 40 mM acetic acid already died on the first day while the other concentrations showed no effects on the viability of the cell line. As expected, the control cells showed a filament-like mitochondrial network (FIG. 14, A+B) while the cells in the two low acetic acid concentrations had network swellings with a diameter of up to 1 µm (FIG. 14, F+G and J+K). In the case of the 35 mM acetic acid, it was additionally possible to detect individual mitochondria having a diameter of up to 5 µm (FIG. 14, M+N).

On day 2, the control and the cell line in 25 mM acetic acid showed no modifications worth mentioning (FIG. 14, C+D and G+H), few mitochondria of the cells in 30 mM acetic acid had diameters of 4 µm (FIG. 14, K+L). The cells with the maximum acetic acid concentration showed giant mitochondria which increased in size even further compared to the day before and in part had diameters of 7 µm. At the same time, some of the cells still showed a tubular network (FIG. 14, O+P).

Example 13

Results of the Methods for the Transfection of Mitochondria with Mitochondrial Expression Plasmids

13.1. Particle Bombardment with the Gene Gun

13.1.2. Determination of the Implementing Provisions

In order to define the variables, a comparison was made with respect to the cytoplasmic transfection of the subsequently used 143B.TK− cell line. In initial preliminary tests, the scatter behavior of the particles was studied depending on the employed insertion level (A-D). In this connection, it turned out that when the lowermost level (D) was used, many gold particles were distributed beyond the edge of the employed 35 mm culture dishes. An insertion of the culture dish carrier on the uppermost level (A) directly below the macrocarrier holder resulted in a hit pattern where only a circular region having a diameter of approximately 1 cm was hit by the gold particles in the center of the dish. In this region, the particles were so close that—either by the suddenly acting helium beam or directly by the strike of the particles—no more cells could be found. In the next level (B) underneath, a similar but weakened effect could be observed: The gold particles could only be found in a region having a diameter of approximately 2 cm and here, too, it turned out that a majority of the cells was removed or destroyed in this region. When the second lowermost level (C) was used, the amount of the removed cells was much lower and the gold particles showed a more homogenous distribution pattern over almost the entire surface of the culture dish. However, it was still possible to detect a small area in the center of the dish where the gold particles were found in a rather high concentration. Since here the best results with respect to the particle distribution and the survival rate of the cells could be obtained, all subsequent experiments using a culture dishes were carried out at this level.

Figure 2C:
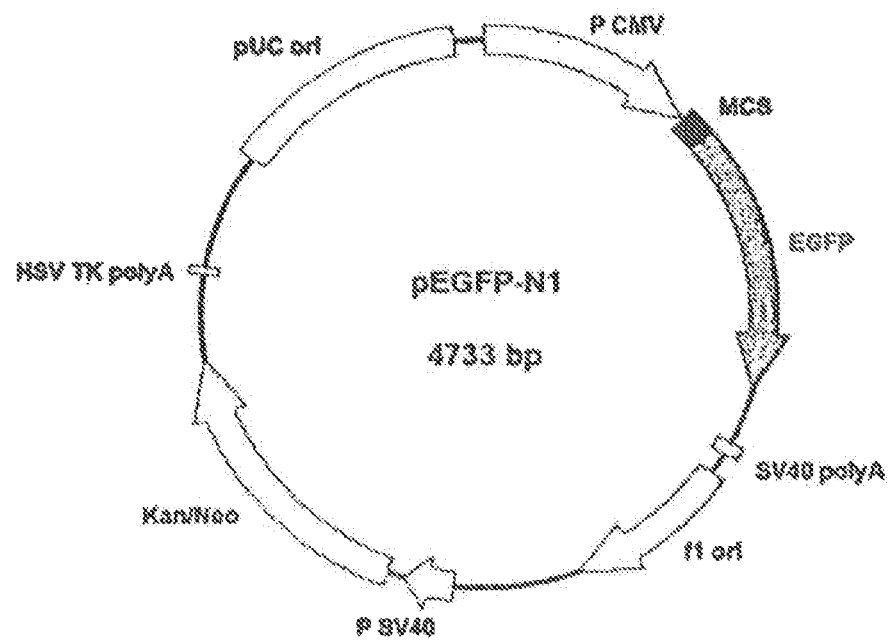
FIG. 2C shows the vector map of pEGFP-N1. The vector pEGFP-N1 of Clontech company enables the expression of a fusion protein, at the N-terminus of which EGFP is localized. If the vector is used without sequences introduced by cloning, the EGFP is visible in the entire cytoplasm and the cell nucleus.

In the next step, the combination of applied partial vacuum (in Hg, inches of mercury) and the applied rupture disk pressures (in psi, pounds per square inch) was optimized. For this purpose, two 35 mm culture dishes with cells (about 40-60% confluence) were bombarded in each case with 600 µg of the gold particles which had a diameter of 0.6 µm and had been coated beforehand with 600 ng of the pEGFP-N1 plasmid (FIG. 2C). For comparing the transfection rate with conventional methods, a culture dish was additionally transfected with the FuGENE® HD reagent (company of Roche, Mannheim, Germany). After all combinations of 15, 20, 25 and 27 in Hg partial vacuum and the rupture disks for 1350, 1500, 1800 and 2000 psi were applied, the examination under a fluorescence microscope was conducted the next day. In each case, a plurality of fluorescence and phase contrast images was made and then the transfected cells and the total number of cells were determined therewith. The results of this count and the transfection rates calculated therefrom are listed in table 4 below:

TABLE 4

Determination of the transfection rate under different reaction conditions

| Test conditions (rupture disk/ partial vacuum) | Total number of the cells | Number of the transfected cells | Transfection rate |
| --- | --- | --- | --- |
| 1350 psi/15 in Hg | 13534 | 3 | 0.022% |
| 1550 psi/15 in Hg | 13038 | 4 | 0.031% |
| 1800 psi/15 in Hg | 13700 | 5 | 0.036% |
| 2000 psi/15 in Hg | 13886 | 7 | 0.050% |
| 1350 psi/20 in Hg | 19014 | 12 | 0.063% |
| 1550 psi/20 in Hg | 21808 | 16 | 0.073% |
| 1800 psi/20 in Hg | 18730 | 16 | 0.085% |
| 2000 psi/20 in Hg | 18828 | 9 | 0.048% |
| 1350 psi/25 in Hg | 15492 | 23 | 0.148% |
| 1550 psi/25 in Hg | 14560 | 65 | 0.446% |
| 1800 psi/25 in Hg | 20572 | 95 | 0.462% |
| 2000 psi/25 in Hg | 17810 | 61 | 0.343% |
| 1350 psi/27 in Hg | 2888 | 85 | 2.94% |
| 1550 psi/27 in Hg | 2179 | 140 | 6.42% |
| 1800 psi/27 in Hg | 3846 | 310 | 8.06% |
| 2000 psi/27 in Hg | 3848 | 127 | 3.79% |
| FuGENE ® HD | 20102 | 4372 | 24.7% |

Figure 15:
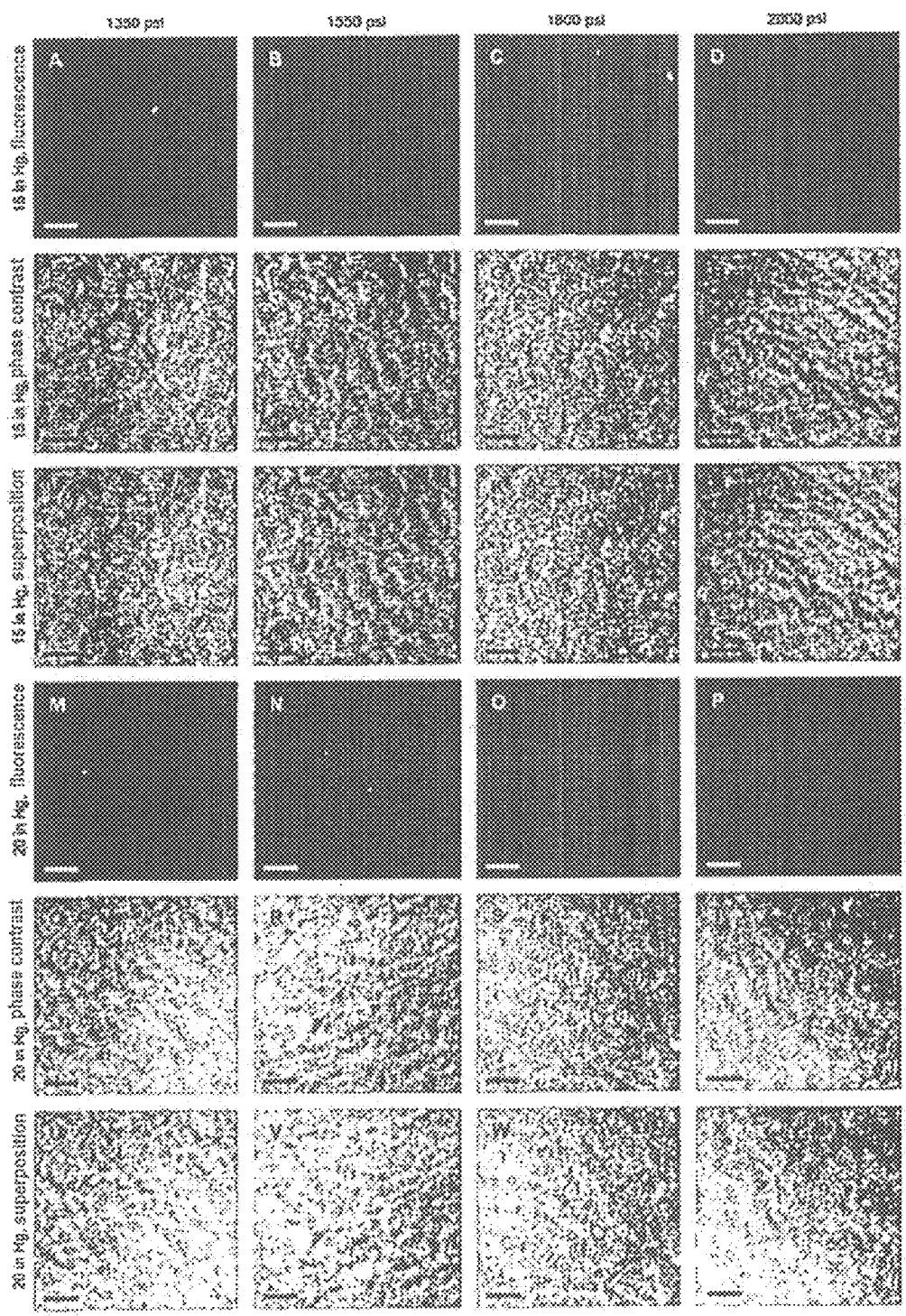
FIG. 15 shows the optimization of the test parameters to use the gene gun, 15 and 20 in Hg. A-D or M-P: fluorescence images of the cell line 143B.TK−: E-H or Q-T: phase contrast images; I-L or U-X: superposition from fluorescence and phase contrast images. The calibration marks correspond to 100 μm.

With a chamber vacuum of 15 in Hg, only some few transfected cells could be found (FIG. 15, A-D). The transfection rates thus only achieved very low values which increased at an increasing bombardment pressure from 0.022 to 0.050%. The increase in the chamber vacuum to 20 in Hg only resulted in minor improvement: The transfection rates varied between 0.048 and 0.085%, which could also be seen on the corresponding images (FIG. 15, M-P) by means of some few transfectants. It turned out again that the transfection rate increased with increasing pressure but dropped to the minimum value when the strongest rupture disks (2000 psi) were used.

Figure 16:
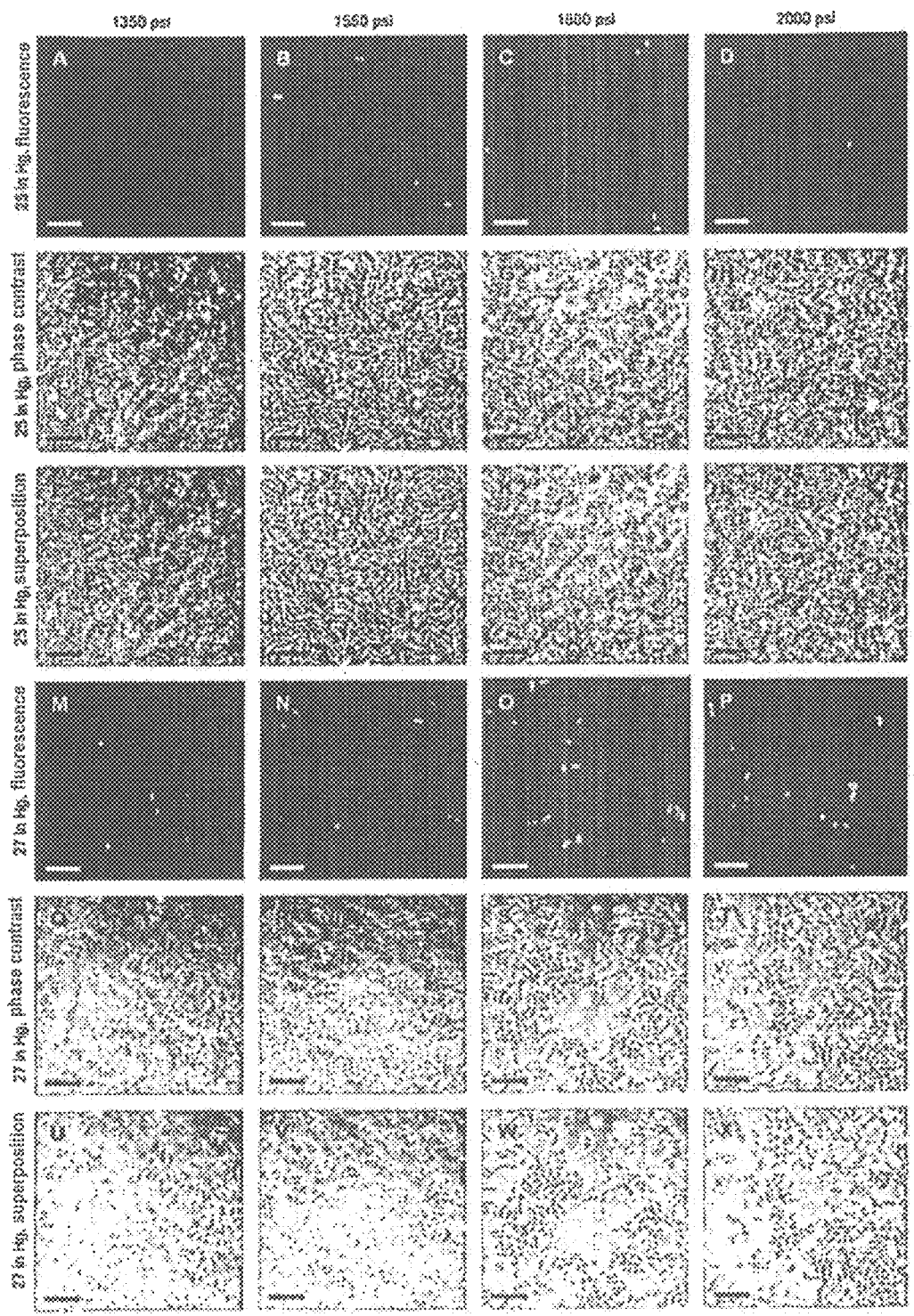
FIG. 16 shows the optimization of the test parameters to use the gene gun, 25 and 27 in Hg. A-D or M-P: fluorescence images of the cell line 143B.TK−: E-H or Q-T: phase contrast images; I-L or U-X: superposition from fluorescence and phase contrast images. The calibration marks correspond to 100 μm.

With chamber vacuum of 25 in Hg, an increased number of green cells were seen on the fluorescence images (FIG. 16, A-D) and also the transfection rate increased correspondingly up to 0.462% at a bombardment pressure of 1800 psi. Due to the use of the maximum chamber vacuum of 27 in Hg, the transfection rate could be increased once again by a factor of approximately 20: Values between 2.94% were achieved when rupture disks for 1350 psi were used and 8.06% were achieved with 1800 psi rupture disks. This could also be confirmed by studying the fluorescence images (FIG. 16, M-P).

Figure 17:
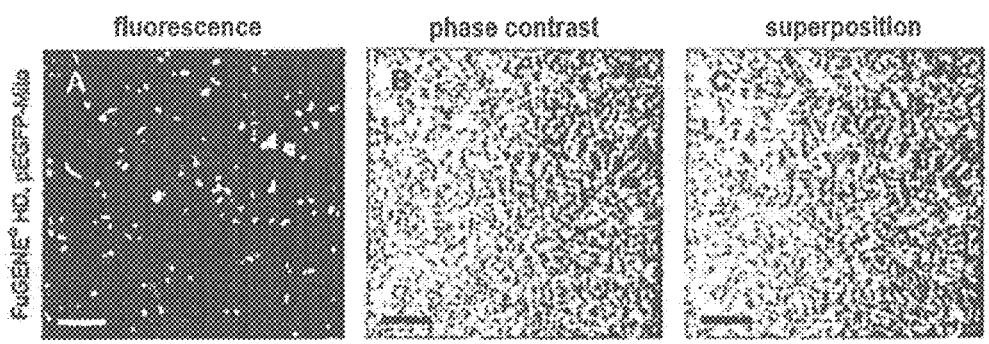
FIG. 17 shows the comparison transfection rate of FuGENE® HD. The calibration marks correspond to 100 μm.

Compared thereto, the use of the FuGENE® HD transfection reagent supplied a once again 3 times higher transfection rate of 24.7% (FIG. 17).

On account of these results, the further transfection experiments were carried out using the gene gun with the following parameters:
use of the second level from below,
chamber vacuum of 27 in Hg,
use of rupture disks for 1800 psi.

13.1.3. Induction of Megamitochondria

Since mitochondria only have a diameter from 0.5-1 µm, it is almost impossible to hit them in living cells by gold particles of 0.6 m in such a way that the DNA on the gold particles reaches the mitochondria matrix.

Figure 18:
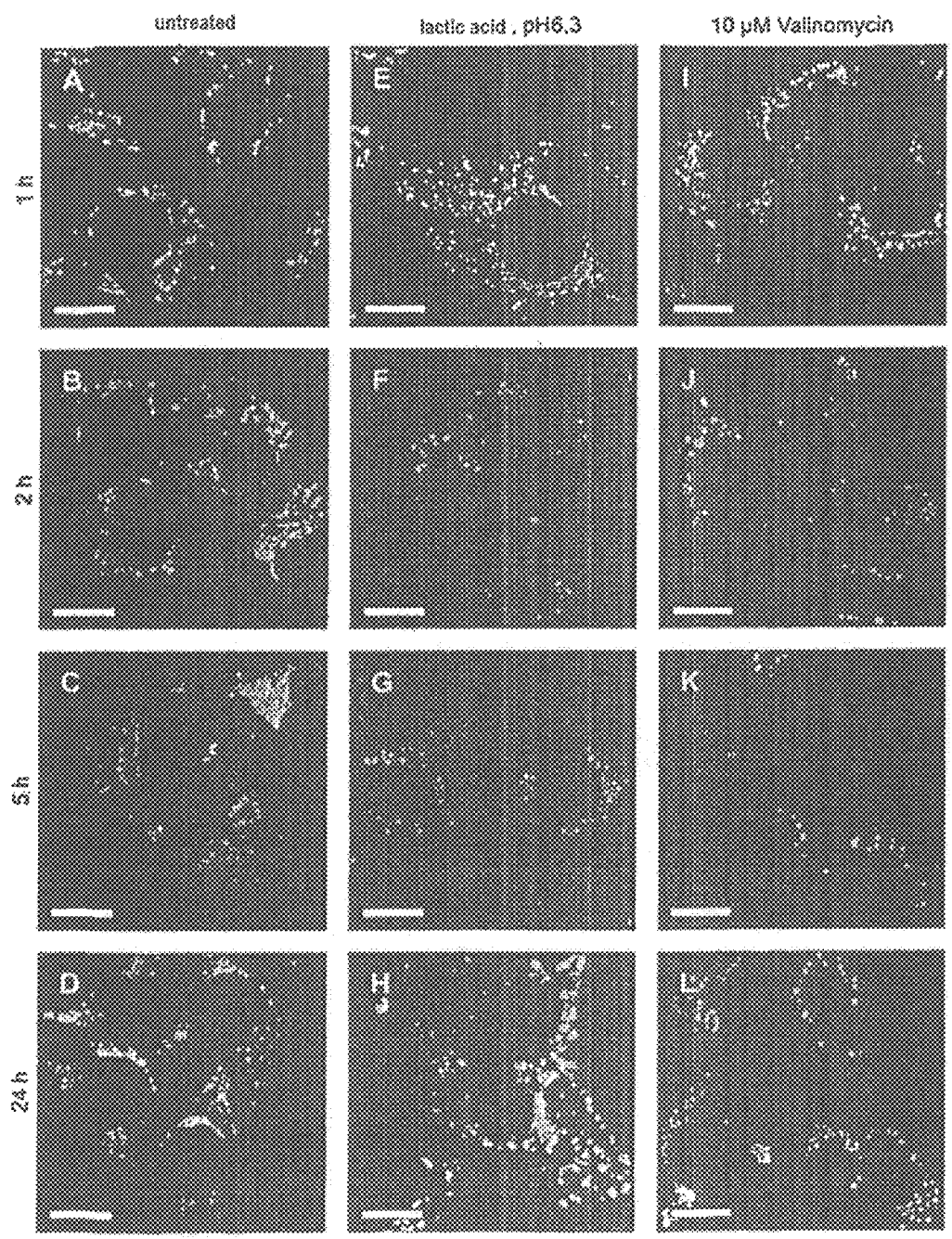
FIG. 18 shows the induction of megamitochondria by lactic acid medium or the addition of valinomycin. Fluorescence images, A-D: 143B.TK⁻ +pEGFP-Mito in normal culture medium, E-H: 143B.TK⁻ +pEGFP-Mito in culture medium adjusted to a pH of 6.3 using lactic acid, I-L: 143B.TK⁻ +pEGFP-Mito in culture medium with 10 μM valinomycin. The calibration marks correspond to 100 μm.

It was initially tested what method is most suitable to induce megamitochondria with the gene gun prior to the transfection experiments. For this purpose, the stable cell line 143B.TK$^-$ +pEGFP-Mito, which has green mitochondria, was cultured for one day, on the one hand, in culture medium adjusted by lactic acid to a pH of 6.3 and, on the other hand, with culture medium which contained 10 M valinomycin. As a control, the same cell line was used in unmodified culture medium. After one, two, five and 24 hours, an examination was conducted under the fluorescence microscope. The mitochondria in the control cell line showed no morphology changes in the first five hours—they formed a network without swellings worth mentioning (FIG. 18, A-C). After one day, however, the culture medium had adopted a slightly orange color and some of the mitochondria were spherically swollen or thickened (FIG. 18, D). In the cell line treated with lactic acid, the entire mitochondrial network was dissolved after one hour and it was only possible to detect spherical mitochondria, part of which already showed an enlargement (FIG. 18, E). In the following hours and on the next day, another increase in size could be identified, and therefore the megamitochondria were clearly detectable (FIG. 18, F-H). The addition of valinomycin also induced spherical mitochondria after only one hour. However, said mitochondria were somewhat larger than in the lactic acid medium, which was also the case after two hours (FIG. 18, I+J). After five and/or 24 hours, almost no differences in the mitochondrial size could be determined between the test series (FIG. 18, K+L).

Figure 19:
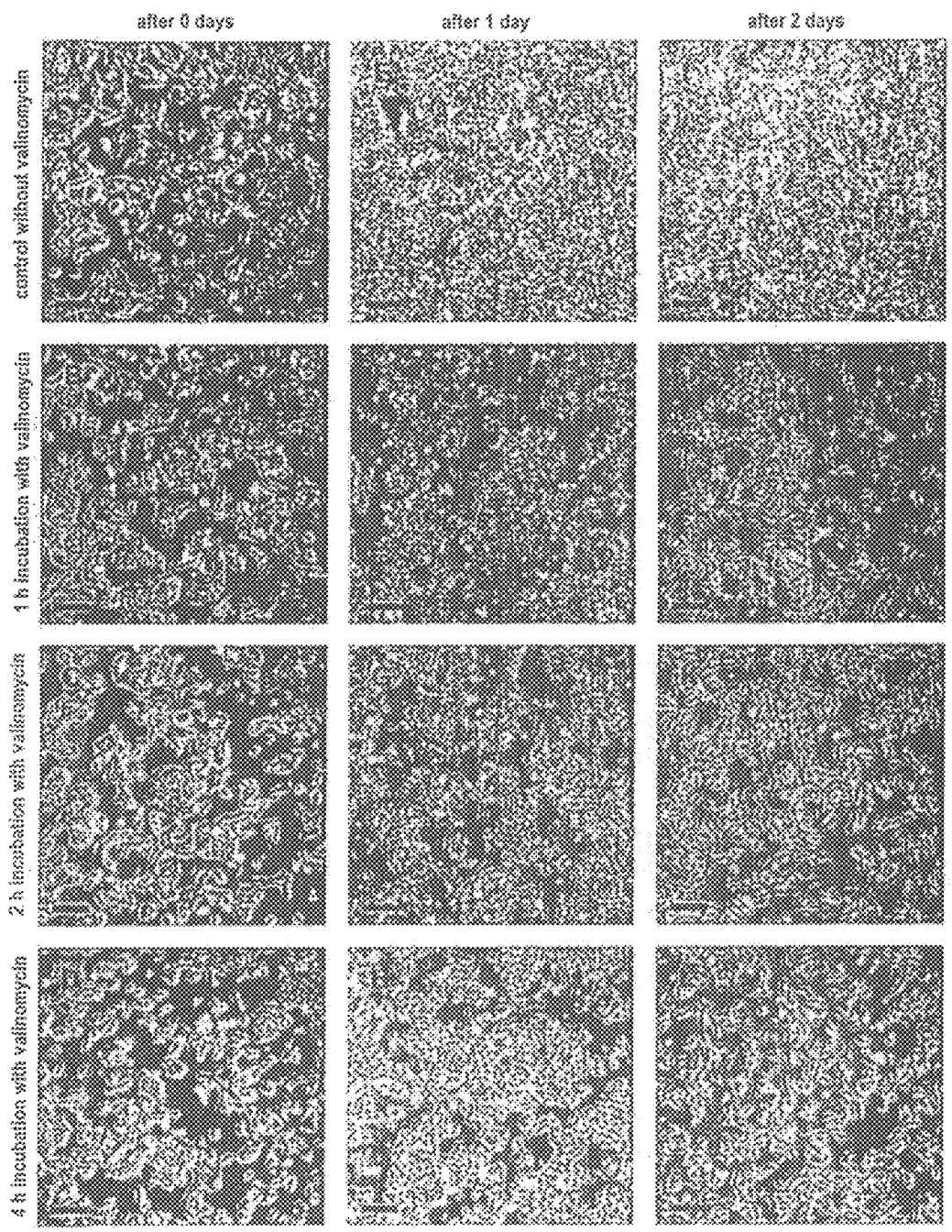
FIG. 19 shows the growth inhibition by treatment with valinomycin. Phase contrast images, A-C: 143B.TK⁻ without valinomycin treatment, D-F: 143B.TK⁻ after one hour of valinomycin treatment, G-I: 143B.TK⁻ after 2 hours of valinomycin treatment, J-L: 143B.TK⁻ after 4 hours of valinomycin treatment. The calibration marks correspond to 100 μm.

A study of the cell line treated with valinomycin revealed that the cells had almost not proliferated after 24 hours. Since this might create problems in the following transfection, a test series was carried out where the 143B.TK$^-$ cell line was incubated in culture medium with 10 µM valinomycin for one, two and four hours. The same cell line in valinomycin-free medium served as a control. After the incubation, the cells were washed in normal culture medium three times for 10 minutes to remove the valinomycin. Following the wash steps, images were taken under the microscope to document the initial density of the cells (FIG. 19, A-D). On the following two days, new images were made. Here, it turned out that regardless of the incubation period all cells treated with valinomycin virtually stopped dividing—in contrast to the control cells (FIG. 19, E-H). The images of the second day after the incubation even showed a decrease in the cell density, which supported the conclusion that some of the cells died after the valinomycin treatment (FIG. 19, I-L). The rapid induction of megamitochondria by valinomycin would be desirable but on account of these observations an induction of megamitochondria by the addition of valinomycin to the culture medium was initially disregarded since it was not known whether this might influence the transfection result.

Another test series should study whether the duration of the incubation in acidified medium had an influence on the subsequent transfection with the gene gun. It here turned out that an incubation for more than two hours resulted in an increased removal of the cells when bombarded with gold particles. This is why the cells were treated with lactic acid medium in the following experiments for approximately 60 to 120 minutes prior to the test onset.

Figure 20:
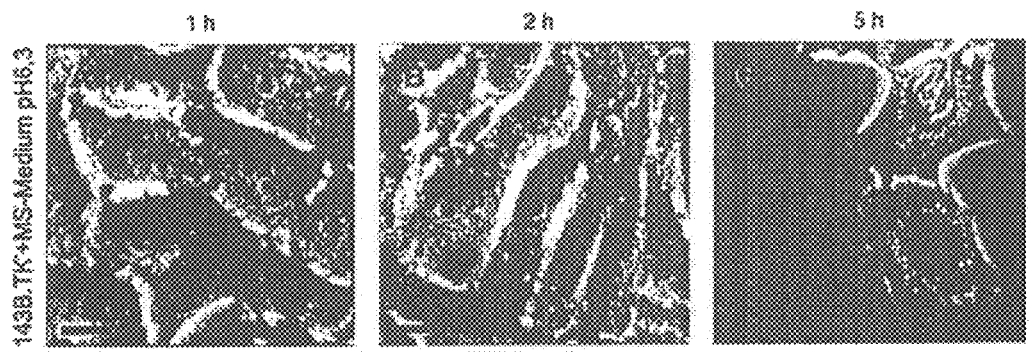
FIG. 20 shows the visibility of the megamitochondria in the phase contrast. Phase contrast images of 143B.TK⁻ in a culture medium adjusted to a pH of 6.3 using lactic acid. The calibration marks correspond to 10 μm.

After this time, the enlarged mitochondria were already visible in the phase contrast (FIG. 20, A+B). After five hours of incubation, they were even better visible, as expected on the basis of the results of the preceding test series (FIG. 20, C).

13.1.4 Transfection with mtDNA

Figure 21:
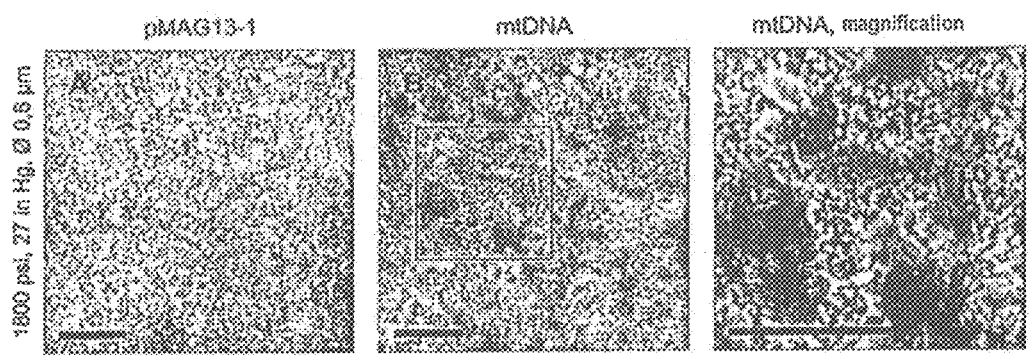
FIG. 21 shows the aggregation of the gold particles by mtDNA. Phase contrast images of gold particles after the bombardment of a culture dish. A: with pMAG13-1 coated gold particles as a control, B: with mtDNA coated gold particles, C: enlargement of B. The calibration marks correspond to 30 μm.

At the beginning, 1 µg of cesium chloride gradient-purified mtNDA was used for each transfection batch with 0.5 µg gold particles having a diameter of 0.6 µm. A strong aggregate formation was already seen during the coating of the gold particles and could also be identified on the culture plate by means of a light microscope after the bombardment of the $\rho^0$ cell line 143B.TK$^-$ K7. In comparison with gold particles coated with the plasmid pMAG13-1 (FIG. 21, A), the use of mtDNA markedly revealed a formation of large aggregates (FIG. 21, arrows at B+C). The distribution of the gold particles was largely confined to an area having a diameter of 1-1.5 cm in the center of the culture dish where the cells were also very strongly detached. In order to reduce this aggregate formation which was presumably dependent on the DNA, the amount of the mtDNA was reduced to 0.5 µg for each transfection batch, and therefore a slight improvement actually occurred. Gold particles having a diameter of 1.0 or 1.6 µm were also tested. A further slight reduction in the aggregation could here be found as well. On account of these results, 18 transfections with 0.5 µg mtDNA and 0.5 µg gold particles having the three listed diameters were conducted in each case. After one day of cultivation in $\rho^0$ medium, the cells were transferred to 150 mm culture dishes and continued to be cultured in $\rho^0$ selection medium. However, no living clones could be found after three to four weeks each.

13.1.5. Transfection with Mitochondrial Expression Vectors

Prior to the beginning of the respective test series, five 35 mm culture dishes each were transfected with the employed plasmid and the FuGENE® HD transfection reagent to be able to exclude a contamination of the DNA preparation with other EGFP-expressing vectors. If no green fluorescent cells were found on the next day, the DNA preparation could be used for the transfection tests with the gene gun.

For each transfection batch, 1 µg of the respective plasmid and 0.5 µg gold particles having a diameter of 0.6 µm were used. In order for the cells to be still well observable after 1.5-2 days, culture dishes were used where the cells had approximately a confluence of 50-60%. For the purpose of assessment, each dish was fully searched for fluorescence signals under the fluorescence microscope having a magnification of 200 times two days later. Since it was not known how strong the expression of the mtEGFP gene was, the period up to the observation was intentionally chosen to be long.

Figure 22:
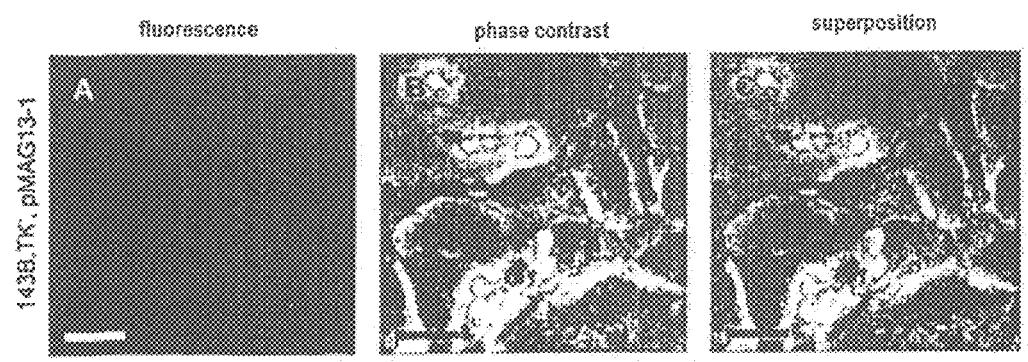
FIG. 22 shows fluorescent mitochondria after gene gun bombardment with pMAG13-1. A: fluorescence image (enhanced) of the cells, B: phase contrast image of the cells, C: superposition of A and B. The calibration marks correspond to 20 μm.

At the beginning, the plasmid pMAG12-1 was used, by means of which a total of 66 culture dishes was treated with the cell line 143B.TK$^-$. However, no cells with fluorescent mitochondria were found. When the pMAG13-1 plasmid was complete, the transfection experiments with pMAG12-1 were stopped. The vector pMAG13-1 additionally contained another replication origin for the L-strand, and therefore a proliferation could take place inside the mitochondria so as to enable an increase in the expression. The plasmid was used under the same conditions as its predecessor pMAG12-1 for the transfection experiments. The cell line 143B.TK$^-$ was used again and was treated 96 times. When the plates were searched, it was possible to discover very weak fluorescence signals which after a comparison with the corresponding phase contrast image revealed a localization of the signals in the mitochondria of the cell (FIG. 22). However, two days later, the cells were no longer detectable.

In order to subject the cells or the mitochondria to a selection pressure for the introduced plasmids, another mitochondrial expression vector was used: In the pMAG14-1 plasmid, a 16S rRNA gene was integrated in addition to the genes of the pMAG13-1 plasmid and conveys a resistance to the antibiotic chloramphenicol.

After the treatment of 72 dishes of the cell line 143B.TK$^-$, no fluorescent mitochondria could be found. The simultaneous addition of chloramphenicol into the culture medium allowed the use of an additional screening method which corresponded to the selection of $\rho^0$ cells transfected with mtDNA. The cells were transferred to 150 mm dishes and after a cultivation of two to three weeks in the selection medium were searched for clones using chloramphenicol. However, no transfectants were detected with this method. In order to further enhance the expression of the mtEGFP, vectors were then developed where the mtEGFP gene should be transcribed by the highly processive T7-RNA polymerase. In a first step, it was tried to transfect by means of the gene gun the plasmid pCRII-TOPO mtEGFP (FIG. 9) into cells which expressed the T7-RNA polymerase with an N-terminal mitochondrial signal sequence in the nucleus. In the case of a successful transfection, the T7-RNA polymerase imported into the mitochondria would thus transcribe the mtEGFP gene on the plasmid and a fluorescence signal would be visible.

The plasmid was used in accordance with the formerly used mitochondrial expression plasmids in 60 transfection experiments, however, no transfected cells were found under the fluorescence microscope here as well.

Figure 23:
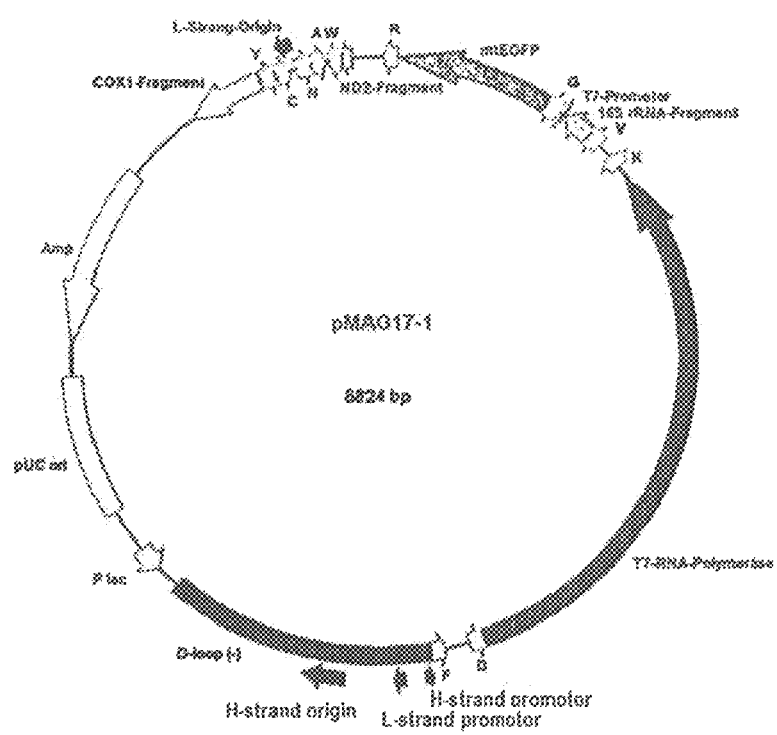
FIG. 23 shows the vector map of pMAG17-1.

Then, the plasmids pMAG17-1 (FIG. 23) and pMAG14-3 were used in the transfection experiments, which both contained the gene for the T7-RNA polymerase under the control of the mitochondrial H-strand promotor. In connection with these two plasmids—similar to the transfection experiments with the mitochondrial DNA—an aggregation of the gold particles manifested itself which was, however, not very strong and could be fully prevented by the reduction of the DNA amount used for each experiment. Correspondingly, only 0.5 µg plasmid DNA was used on 0.5 µg gold particles. When 78 dishes had been treated with the plasmid pMAG17-1 (FIG. 23), it was again not possible to find any transfectants and the process was continued with the plasmid pMAg14-3 which additional contained the 16S rRNA gene for the chloramphenicol resistance. After 66 transfection experiments, no fluorescent mitochondria were discovered with this plasmid under the fluorescence microscope, and the selection for the chloramphenicol resistance also ended without a positive result.

13.2. Transfection with Magnetic Particles

In the experiments carried out on the basis of the present invention with MATra-A, the megamitochondria were induced by one day of incubation in a culture medium adjusted to a pH of 6.3 with lactic acid (see example 13.1.3) in 35 mm culture dishes. Then, the actual transfection was carried out with 3 µg of the corresponding plasmid.

Figure 24:
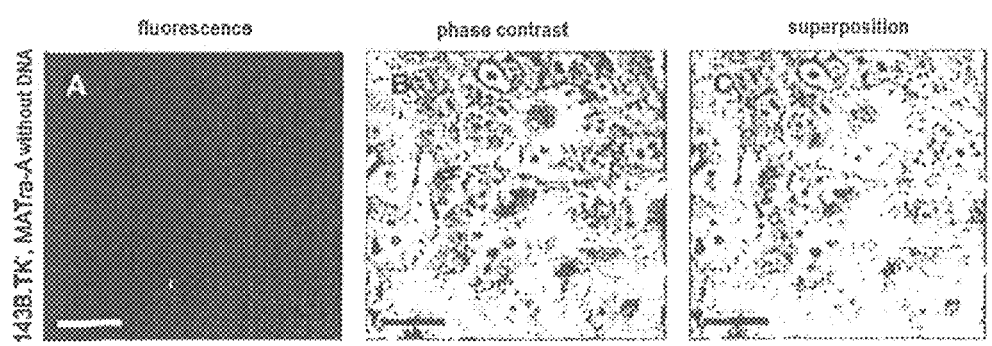
FIG. 24 shows the fluorescence of the MATra-A particles. Images of MATra-A particles without DNA on 143B.TK⁻ cells, A: fluorescence image, B: phase contrast image, C: superposition of A and B. The calibration marks correspond to 20 μm.

After the transfection with the plasmid pMAG13-1, slightly green structures could be discovered under the fluorescence microscope throughout the dish after two days. Since the intensity of the fluorescence signals, expected after the gene gun experiments, was also only very low, these structures were investigated in more detail. On account of comparisons with the corresponding phase contrast images, the particles were suspected of triggering the fluorescence. After the use of MATra-A particles without plasmid DNA, these structures could again be discovered in or on the cells (FIG. 24), which confirmed this assumption.

On account of these observations, the cells transfected with MATra-A were not studied for the expression of the mtEGFP gene. Then, 25 transfections were conducted with the plasmid pMAG14-1 which can convey a chloramphenicol resistance. After the transfer of the cells to 150 mm culture dishes, it was, however, not possible to identify any chloramphenicol-resistant clones after a further cultivation for three to four weeks.

13.3. Transfection by Microinjection of DNA

Figure 25:
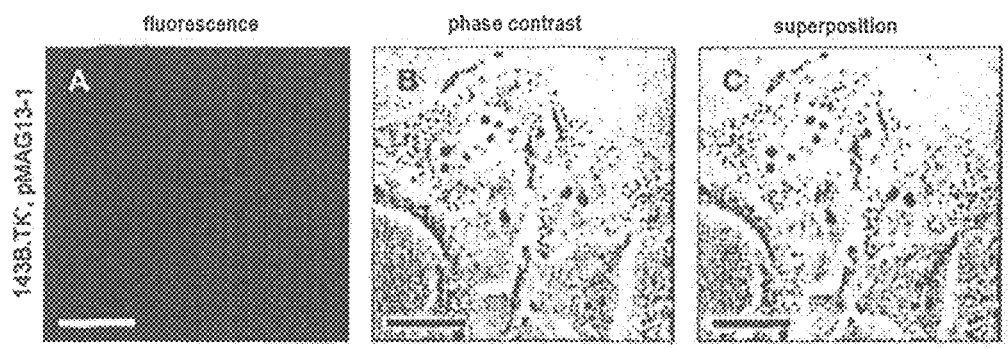
FIG. 25 shows fluorescent mitochondria after microinjection with pMAG13-1. A: fluorescence image (enhanced) of the cells, B: phase contrast image of the cells, C: superposition of A and B. The calibration marks correspond to 20 μm.

The cell line 143B.TK$^-$ was seeded on glass bottom dishes and the megamitocnodria were induced using sodium acetate (example 12.1). The plasmid pMAG13-1 was used in concentrations of 50-350 ng/µl, wherein the injection settings were also varied. After the injection, the cells were further cultured with antibiotics to minimize possible contaminations by the injection on the open dish. The next day, the culture dishes were searched for transformants under the fluorescence microscope. It was possible to discover very weak signals in the interior of cells, which implied a successful transfection of mitochondria (FIG. 25). Injection experiments with mitochondrial DNA in $\rho^0$ cells were not carried out since it was not possible in these cells to induce megamitochondria in corresponding size.

The invention is further described by the following numbered paragraphs:

1. A mitochondrial expression vector, comprising a gene to be expressed and/or a selection marker, and a mitochondrial promoter region.
2. A method for introducing a DNA to be expressed into mitochondria of mammalian cells, wherein the method comprises the steps of:
    (i) construction of a mitochondrial expression vector according to paragraph 1 or a mitochondrial genome,
    (ii) reversible induction of megamitochondria and
    (iii) transfection of megamitochondria by means of a physical transfection method.
3. The method according to paragraph 2, wherein the megamitochondria are reversibly induced by acidification of the culture medium comprising the mammalian cells.
4. The method according to paragraph 3, wherein the culture medium is acidified by the addition of lactic acid, lactate, sodium acetate and/or acetic acid or mixtures thereof.
5. The method according to paragraph 4, wherein the pH in the culture medium is set for the purpose of acidification to between 5.7 and 7.0, preferably between 6.3 and 7.0.
6. The method according to paragraph 4, wherein the concentration of lactic acid, sodium acetate and/or acetic acid in the culture medium is after the acidification between 5 and 100 mM, preferably between 40 and 70 mM for lactic acid, preferably between 50 and 60 mM for sodium acetate and preferably between 30 and 35 mM for acetic acid.
7. The method according to any of paragraphs 2 to 6, wherein the DNA to be expressed is exogenous DNA, complete mitochondrial DNA and/or the derivatives thereof.
8. The method according to any of paragraphs 2 to 7, wherein the physical transfection method is selected from the group consisting of the bombardment of the cells with DNA-coated microparticles in a gene gun, the transfection by means of magnetic particles and the microinjection.
9. The method according to paragraph 8, wherein prior to the bombardment of the mammalian cells with DNA-coated microparticles in a gene gun or prior to the transfection by means of magnetic particles, the megamitochondria are reversibly induced by acidifying the culture medium using the addition of lactic acid.
10. The method according to paragraph 8 or 9, wherein prior to the microinjection of the mammalian cells, the megamitochondria are reversibly induced by acidifying the culture medium by means of the addition of sodium acetate or acetic acid.
11. The method according to any of paragraphs 2 to 10, wherein the mitochondrial expression vector comprises a mitochondrial promotor region and a gene to be expressed or consists of the complete mitochondrial genome or comprises derivatives thereof.
12. A method for the reversible induction of megamitochondria of mammalian cells by acidifying the culture medium containing the mammalian cells by the addition of sodium acetate or lactic acid.
13. The method according to paragraph 12, wherein the concentration of sodium acetate or acetic acid in the culture medium is after the acidification between 5 and 100 mM, preferably between 50 and 60 mM for sodium acetate and preferably between 30 and 35 mM for acetic acid.
14. A method for the transfection of megamitochondria of mammalian cells by means of a physical transfection method, wherein the physical transfection method is selected from the group consisting of the bombardment of the cells with DNA-coated microparticles in a gene gun, the transfection by means of magnetic particles and the microinjection.
15. The method according to paragraph 14, wherein prior to the bombardment of the mammalian cells with DNA-coated microparticles in a gene gun or prior to the transfection by means of magnetic particles the megamitochondria are reversibly induced by the acidification of the culture medium by the addition of lactic acid.

Having thus described in detail preferred embodiments of the present invention, it is to be understood that the inven- tion defined by the above paragraphs is not to be limited to particular details set forth in the above description as many apparent variations thereof are possible without departing from the spirit or scope of the present invention.

What is claimed is:

1. A method for introducing a DNA to be expressed into mitochondria of mammalian cells, wherein the method comprises the steps of:
   (i) constructing a mitochondrial expression vector, comprising a gene to be expressed and/or a selection marker and a mitochondrial promoter region, or a mitochondrial genome,
   (ii) reversibly inducing the mitochondria of mammalian cells into megamitochondria wherein the inducing comprises acidifying culture medium comprising the mammalian cells by adding sodium acetate and
   (iii) microinjecting the mitochondrial expression vector into the megamitochondria.

2. The method according to claim 1, wherein the pH of the culture medium is between 5.7 and 7.0.

3. The method according to claim 2, wherein the pH in the culture medium is between 6.3 and 7.0.

4. The method according to claim 1, wherein the concentration of sodium acetate in the culture medium is between 5 and 100 mM.

5. The method according to claim 4, wherein the concentration of sodium acetate in the culture medium is between 50 and 60 mM.

6. The method according to claim 1, wherein the DNA to be express is exogenous DNA or complete mitochondrial DNA.

7. The method according to claim 1, wherein the mitochondrial expression vector comprises a mitochondrial promoter region and a gene to be expressed or consists of the complete mitochondrial genome.

* * * * *

```
                         SEQUENCE LISTING

<160> NUMBER OF SEQ ID NOS: 8

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      Synthetic oligonucleotide - Primer EGFP-001-FOR

<400> SEQUENCE: 1
cttttggtct caatgatggt gagcaaggg                                      29

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      Synthetic oligonucleotide - Primer EGFP-716-REV

<400> SEQUENCE: 2
gttagtggtc tctatttgta cagctcgtcc                                     30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      Synthetic oligonucleotide - Primer EGFP-156-FOR

<400> SEQUENCE: 3
caagctgccc gtgccctgac ccaccctcgt gaccac                              36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      Synthetic oligonucleotide - Primer EGFP-191-REV

<400> SEQUENCE: 4
gtggtcacga gggtgggtca gggcacgggc agcttg                              36

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      Synthetic oligonucleotide - Primer 01562-FOR

<400> SEQUENCE: 5
gcgctgcagt aacatggtaa gtgtactgga aagtgcac                            38

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      Synthetic oligonucleotide - Primer 03351-REV
```

<400> SEQUENCE: 6

```
aatctcgaga ttagaatggg tacaatgag                                    29
```

<210> SEQ ID NO 7
<211> LENGTH: 720
<212> TYPE: RNA
<213> ORGANISM: Artificial Sequence
<220> FEATURE:
<223> OTHER INFORMATION: Description of Artificial Sequence: Synthetic
      Synthetic polynucleotide - mto-GFP RNA

<400> SEQUENCE: 7

```
augguaucca aaggcgaaga acuauucacc ggcguaguac ccauccuagu agaacuagac    60
ggcgacguaa acggacacaa auucuccgua uccggcgaag gcgaaggcga cgccaccuac   120
ggcaaacuaa cccuaaaauu cauuugcacc accggcaaau acccguacc cugacccacc   180
cuaguaacca cccuaaccua cggcguacaa ugcuucuccc gauaccccga ccacauaaaa   240
caacacgacu ucuucaaauc cgccauaccc gaaggcuaug uccaagaacg aaccaucuuc   300
uucaaagacg acggcaacua caaaacacga gccgaaguaa aauucgaggg cgacacccua   360
guaaaccgaa ucgaacuaaa aggcaucgac uucaaagagg acggcaacau ccuaggccac   420
aaacuagaau acaacuacaa cucccacaac gucuauauca uagccgacaa acaaaaaaac   480
ggcaucaaag uaaacuucaa aauccgacac aacaucgagg acggcuccgu acaacuagcc   540
gaccacuacc aacaaaacac ccccaucggc gacggccccg uacuacuacc cgacaaccac   600
uaccuauccu cccaauccgc ccuauccaaa gaccccaacg aaaaacgcga ccacauaguc   660
cuacuagagu ucguaaccgc cgcaggcauc acccuaggca uagacgaacu auacaaauaa   720
```

<210> SEQ ID NO 8
<211> LENGTH: 239
<212> TYPE: PRT
<213> ORGANISM: Artificial Sequence
<220> FEATURE:
<223> OTHER INFORMATION: Description of Artificial Sequence: Synthetic
      Synthetic amino acid sequence - mto-GFP AS

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Val Asn Phe Lys Ile Arg His Asn Ile Glu Asp Gly Ser
                165             170             175

Val Gln Leu Ala Asp His Tyr Gln Gln Asn Thr Pro Ile Gly Asp Gly
            180             185             190

Pro Val Leu Leu Pro Asp Asn His Tyr Leu Ser Thr Gln Ser Ala Leu
        195             200             205

Ser Lys Asp Pro Asn Glu Lys Arg Asp His Met Val Leu Leu Glu Phe
        210             215             220

Val Thr Ala Ala Gly Ile Thr Leu Gly Met Asp Glu Leu Tyr Lys
225             230             235
```